United States Patent
Maezawa et al.

(10) Patent No.: US 9,372,096 B2
(45) Date of Patent: Jun. 21, 2016

(54) WEARABLE ELECTRONIC APPARATUS, DATA ANALYZER, AND TRAVEL RECORD CONTROL METHOD

(71) Applicant: Seiko Epson Corporation, Shinjuku-ku, Tokyo (JP)

(72) Inventors: Hidekazu Maezawa, Shiojiri (JP); Junichi Otsuka, Matsumoto (JP); Kazunori Shimoda, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/960,768

(22) Filed: Aug. 6, 2013

(65) Prior Publication Data

US 2014/0046588 A1 Feb. 13, 2014

(30) Foreign Application Priority Data

Aug. 7, 2012 (JP) ................................. 2012-175311

(51) Int. Cl.
| | |
|---|---|
| G01C 22/00 | (2006.01) |
| A61B 5/00 | (2006.01) |
| A63B 24/00 | (2006.01) |
| G01S 19/19 | (2010.01) |
| G06Q 10/06 | (2012.01) |

(52) U.S. Cl.
CPC .............. *G01C 22/00* (2013.01); *A61B 5/681* (2013.01); *A63B 24/0062* (2013.01); *G01C 22/006* (2013.01); *G01S 19/19* (2013.01); *G06Q 10/0639* (2013.01)

(58) Field of Classification Search
None
See application file for complete search history.

(56) References Cited

U.S. PATENT DOCUMENTS

| | | | | |
|---|---|---|---|---|
| 5,916,300 | A * | 6/1999 | Kirk et al. ...................... | 701/468 |
| 6,002,982 | A * | 12/1999 | Fry .................. | 701/454 |
| 6,246,362 | B1 * | 6/2001 | Tsubata et al. ................. | 701/491 |
| 6,388,613 | B1 * | 5/2002 | Nagatsuma et al. .......... | 701/469 |
| 6,975,941 | B1 * | 12/2005 | Lau et al. ...................... | 701/491 |
| 8,032,276 | B2 * | 10/2011 | Cawse ......................... | 701/32.4 |
| 2008/0171636 | A1 * | 7/2008 | Usui .................. | A63B 24/0062 482/8 |
| 2011/0032105 | A1 * | 2/2011 | Hoffman et al. ........... | 340/573.1 |
| 2016/0027325 | A1 * | 1/2016 | Malhotra ........... | A63B 24/0006 434/252 |

FOREIGN PATENT DOCUMENTS

JP 2003-322545 A 11/2003

* cited by examiner

*Primary Examiner* — Rami Khatib
*Assistant Examiner* — David Merlino
(74) *Attorney, Agent, or Firm* — Kilpatrick Townsend & Stockton LLP

(57) ABSTRACT

An electronic apparatus refers to location measurement information measured in the past at each time when the latest location measurement information is output from a location measurement module with a predetermined measurement period, if measurement accuracy is good and it is regarded that a direction change has been made, determines the latest location measurement information as saving "necessary" and stores the information. If the measurement accuracy is no good or it is regarded that a positioning point shown by the latest location measurement information is an intermediate point during linear traveling, the latest location measurement information is not saved. Therefore, a data size to be saved is made smaller than that in related art and draining of a battery taken for writing of data is reduced.

8 Claims, 19 Drawing Sheets

ACCUMULATED TRAVEL DISTANCE LA = L12

ACCUMULATED TRAVEL DISTANCE LA = L13

ACCUMULATED TRAVEL DISTANCE LA = L14

ACCUMULATED TRAVEL DISTANCE LA = L15

ACCUMULATED TRAVEL DISTANCE LA = L15 + L56 + L67

WEARABLE ELECTRONIC APPARATUS, DATA ANALYZER, AND TRAVEL RECORD CONTROL METHOD

BACKGROUND

1. Technical Field

The present invention relates to a wearable electronic apparatus including a measurement unit that measures a location, etc.

2. Related Art

In related art, a device that measures an accumulated travel distance using a GPS has been known (for example, Patent Document 1 (JP-A-2003-322545)). The device is used as a wristwatch-type wearable electronic apparatus having a location measurement function of measuring a current location on the earth and called "running watch", "training watch", "runner's watch", or the like. The electronic apparatus has a clock, a GPS receiver, an arithmetic unit, and a memory medium. When a user starts measurement of the location in running, the electronic apparatus automatically and continuously stores location measurement information including periodically measured latitude and longitude. Further, the location information or the like during running stored in the electronic apparatus is analyzed by an external device including a personal computer and used for display of the trajectory of running on a map (map display) and graphical display of changes from the start to the end of the running by computation of parameters including paces and pitches. The user may realize efficient training using the map display and the graphical display.

In wearable electronic apparatuses having the location measurement function such as a running watch, one of the most important requirements is thinness and lightness not to be a burden in running, i.e., "reduction in size and weight". However, there is a trade-off between the reduction in size and weight and the amount of mounting of the memory medium such as an IC memory and the size of a battery (i.e., capacity) that can be mounted. Accordingly, in a known running watch or the like, the data memory capacity and the battery duration are sufficient for running at relatively short distances and short times, but liable to be insufficient for running taking longer required time and long-distance running including a full marathon.

Further, in location measurement using the GPS or the like, it is not necessarily that the location is always measured with accuracy due to various environment factors. If the user linearly moves, the location indicated by the measurement result may fluctuate to right and left or, sometimes the location is measured as if the user has jumped high. On this account, if the location information of the memory points stored in the running watch or the like is used for map display without change, a trajectory more zigzag than the actual running trajectory, and sometimes largely deviating from the actual trajectory may be drawn. Furthermore, when the distance is computed from the displacement of the location of the memory point, an error relative to the actual travel distance occurs.

SUMMARY

An advantage of some aspects of the invention is to realize a wearable electronic apparatus that supports reduction in size and weight and memory of measurement data over long distances.

A first aspect of the invention is directed to a wearable electronic apparatus including a measurement unit that measures a location with a predetermined period, a distance display control unit that performs display control by computing an accumulated travel distance based on measurement results in the measurement unit, a determination unit that determines whether or not the measurement result in the measurement unit is saved with reference to the measurement results in the past at each time of measurement in the measurement unit, a memory control unit that allows a memory unit to store the measurement result in the measurement unit if the determination unit makes a positive determination, and an external output control unit that performs control of outputting data of the measurement result stored in the memory unit to an external device.

As another aspect, the invention may be configured as a travel record control method executed by a wearable electronic apparatus, including measuring a location with a predetermined period, performing display control by computing an accumulated travel distance based on measurement results by the measurement, determining whether or not the measurement result by the measurement is saved with reference to the measurement results in the past at each time of the measurement, allowing a memory unit to store the measurement result by the measurement if the determination as to whether or not the measurement result is saved is a positive determination, and performing control of outputting data of the measurement result stored in the memory unit to an external device (the eighth embodiment).

According to the first aspect and another aspect of the invention, not all of the measurement results measured in the measurement unit are stored, but whether or not the measurement results are saved with reference to the measurement results in the past and only the measurement results determined to be saved are saved, and thus, the size of the data of the series of measurement results from the start to the end of measurement may be made smaller. That is, data to be saved may be thinned. As the data to be saved becomes smaller, power consumption taken for writing of data in the memory unit may be suppressed by the amount. Therefore, even in the case of a wearable electronic apparatus nearly equal to that in related art that has realized reduction in size and weight, storage of the measurement data over the longer distance and the longer period and the reduction in size and weight may be compatible with each other.

A second aspect of the invention is directed to the wearable electronic apparatus described above, wherein the determination unit determines that the measurement result is saved if a direction change condition showing that a movement direction has changed based on the measurement result of the measurement unit is satisfied.

According to the second aspect of the invention, if it is regarded that the movement direction has been changed in the measurement result, a determination of saving may be made. That is, although the data size to be stored and saved in the memory unit is made smaller, the information of the location changed in direction is saved, and thus, even when "map display" in which the travel trajectory is drawn on a map is performed as a data analysis, a trajectory near the actual trajectory may be drawn.

A third aspect of the invention is directed to the wearable electronic apparatus described above, wherein the measurement unit measures the location based on satellite signals and measures at least the movement direction based on Doppler of the satellite signals, and the determination unit determines whether or not the direction change condition is satisfied based on the movement direction measured by the measurement unit.

According to the third aspect of the invention, determination with respect to the direction change may be realized using a known satellite navigation system.

A fourth aspect of the invention is directed to the wearable electronic apparatus described above, wherein the measurement unit determines that the measurement result is not saved if the movement direction measured by the measurement unit and a travel direction based on the locations measured by the measurement unit do not satisfy a predetermined approximate condition.

According to the fourth aspect of the invention, the measurement results judged to have been received in a reception environment in which errors are liable to be contained in the satellite signals may not be saved.

A fifth aspect of the invention is directed to the wearable electronic apparatus described above, which further includes a travel distance memory control unit that allows the memory unit to store the accumulated travel distances at longer time intervals than the predetermined period in a temporal sequence, wherein the external output control unit further outputs data of the accumulated travel distances stored in the memory unit to the external device.

According to the fifth aspect of the invention, the accumulated travel distances may be saved.

A sixth aspect of the invention is directed to the wearable electronic apparatus described above, which further includes a lapse time display control unit that performs display control of a lapse time from a start of computation of the accumulated travel distance, a lapse time memory control unit that allows the memory unit to store the lapse time in correspondence with the measurement result stored by the memory control unit in the memory unit, and a section time information memory control unit that allows the memory unit to store section time information as the lapse time at each time when the accumulated travel distance reaches a predetermined section distance or a time taken for traveling of the section distance, wherein the external output control unit further outputs data of the lapse times and data of the section time information stored in the memory unit to the external device.

According to the sixth aspect of the invention, so-called section measurement may be performed.

A seventh aspect of the invention is directed to a data analyzer including a reception unit that receives data output from the wearable electronic apparatus according to the sixth aspect, and an interpolation unit that, if there is no data of the measurement result corresponding to the section time information among the data received by the reception unit, interpolates and generates the measurement result corresponding to the section time information based on data of sequential lapse times of the section time information and data of the measurement results corresponding to the lapse times.

According to the sixth aspect of the invention, the data necessary for the data analysis of section measurement may not be saved depending on the determination of saving necessity of the measurement results. However, according to the seventh aspect of the invention, even if the measurement result necessary for the section measurement has not been saved, the result may be obtained by using and interpolating the other saved measurement results at the sequential lapse times. Therefore, even in the case where the measurement results to be saved are thinned, data analysis with respect to section measurement may be performed.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
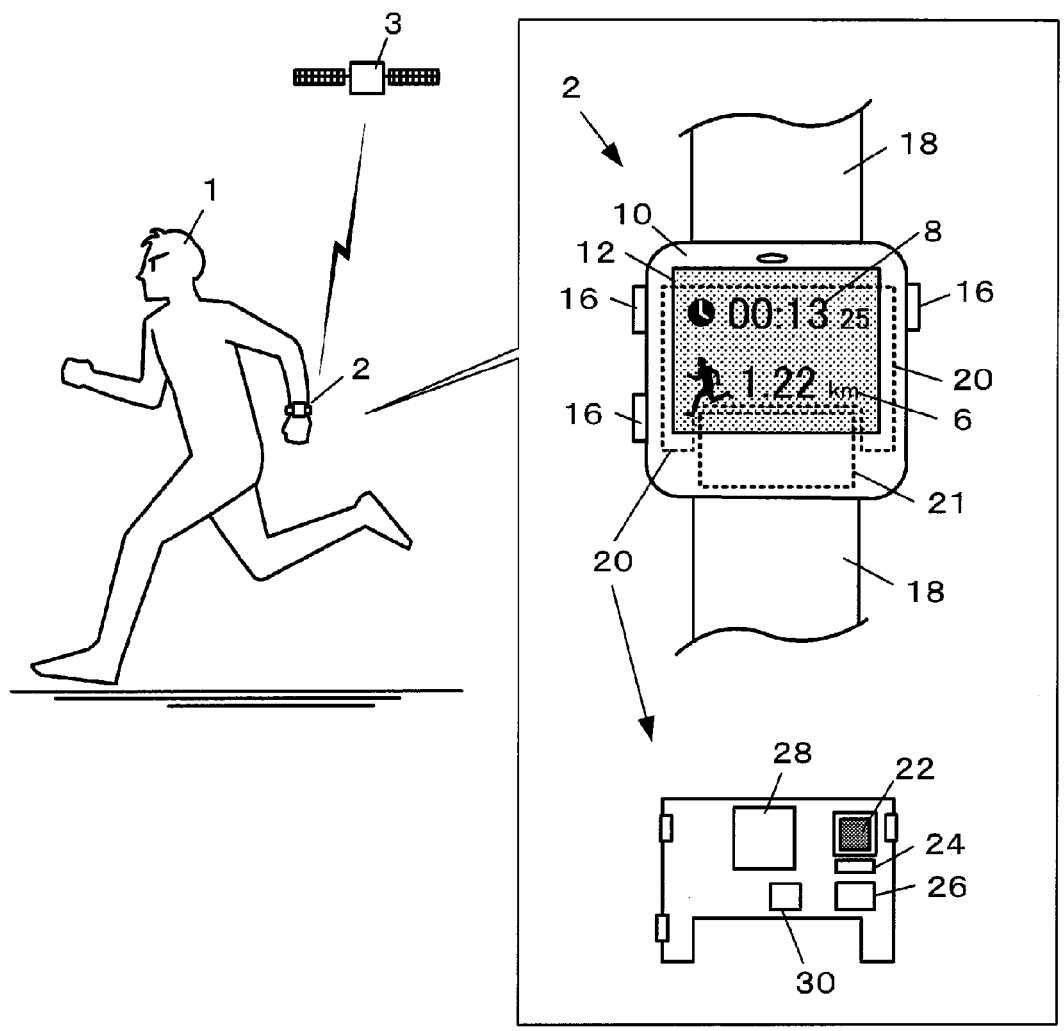
FIG. 1 shows a configuration example of a wearable electronic apparatus.
Figure 2:
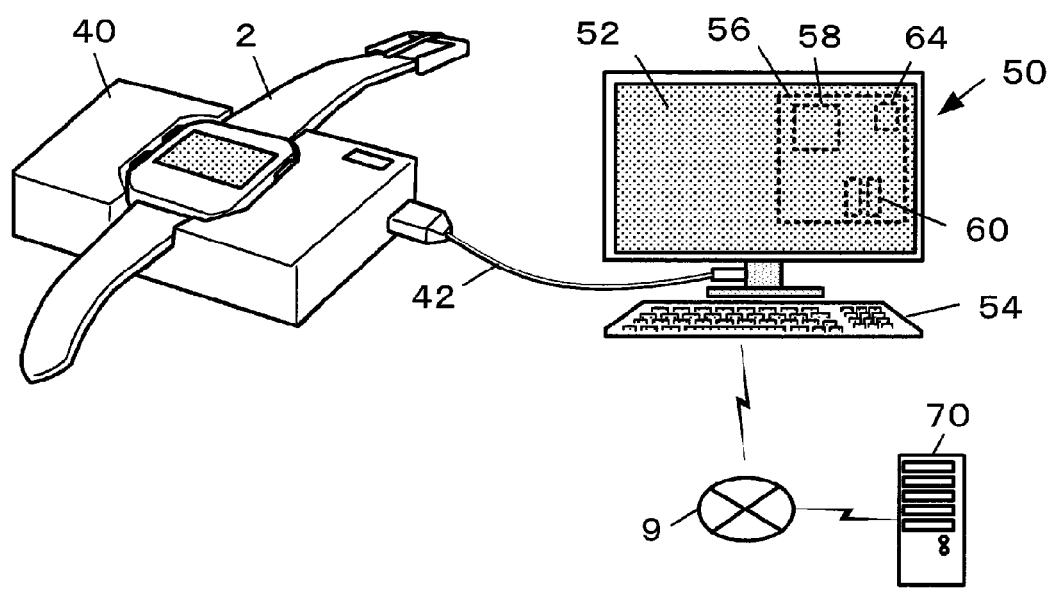
FIG. 2 shows a system configuration example for analysis of data measured and stored in the wearable electronic apparatus.

FIG. 1 shows a configuration example of a wearable electronic apparatus in the embodiment. FIG. 2 shows a system configuration example for analysis of data measured and stored in the wearable electronic apparatus.

As shown in FIG. 1, a wearable electronic apparatus 2 of the embodiment (hereinafter, abbreviated to "electronic apparatus 2") is an apparatus wearable on a wrist or an arm of a user 1 like a wristwatch, and a wearable computer with its appearance classified into a wrist watch or a running watch.

On the upper surface of a main frame 10 of the electronic apparatus 2, a touch panel 12 that can display various training data or the like based on times and location measurement information is provided. Further, on side surfaces of the main frame 10, operation switches 16 for various operation inputs and a band 18 are provided. The band 18 is an attachment piece. This is wrapped around so that the electronic apparatus 2 may be fixed to the wrist or an ankle like a wristwatch.

The main frame 10 forms an airtight chamber, and contains a substrate 20 electrically connected to the touch panel 12 and the operation switches 16 and a rechargeable battery 21 for power supply to the substrate 20 etc. The charging system for the rechargeable battery 21 may be appropriately set. For example, as shown in FIG. 2, the electronic apparatus 2 may be set in a cradle 40 connected to a household power supply, and conducted and charged through the cradle 40 via an electrical contact provided on the rear surface of the main frame 10 or wirelessly charged.

The substrate 20 performs integrative control of the electronic apparatus 2. Specifically, a CPU (Central Processing Unit) 22, a main memory 24, a measurement data memory 26, a location measurement module 28, and a near field communication module 30 are mounted thereon. Further, in addition, ICs including a power supply management IC and a driver IC for the touch panel 12 and electronic components may be appropriately mounted thereon.

The main memory 24 is an information memory medium that may store programs and initial setting data and store operation values of the CPU 22. The memory is realized by appropriately using a RAM, a ROM, or a flash memory.

The measurement data memory 26 is a rewritable nonvolatile memory and a memory medium for storing data of measurement results including location measurement information (hereinafter, referred to as "measurement data"). A flash memory is used in the embodiment, however, another rewritable nonvolatile memory including a ferroelectric memory (Fe RAM) and a magnetoresistive memory (MRAM) may be used.

The location measurement module 28 may receive signals provided from a location measurement system and output the location measurement information with a predetermined period (every second) to the CPU 22. In the embodiment, a GPS (Global Positioning System) is used as the location measurement system. Accordingly, the location measurement module 28 may use known "GPS module", "GPS receiver", etc. "Location measurement information" includes positioning time and date (UTC: Coordinated Universal Time), location coordinates (latitude/longitude), a ground speed (scalar quantity), and a velocity direction (e.g., travel direction with true north at 0°). The ground speed and the velocity direction may be collectively computed as a velocity. Further, the ground speed and the velocity direction are computed based on Doppler shift (also called Doppler) generated in signals transmitted from a GPS satellite. The location measurement information may appropriately include other information.

Note that the system used for location measurement is not limited to the GPS, but another satellite navigation system may be used. Radio waves from base stations in known locations on the ground may be additionally used.

As shown in FIG. 2, the electronic apparatus 2 enables data communication with a data uploading device 50 through wired connection (e.g., connection through a USB cable 42) via the cradle 40. Alternatively, the apparatus may be connected to the data uploading device 50 through wireless communication via the near field communication module 30.

The data uploading device 50 is a device for acquiring the measurement data stored in the electronic apparatus 2 and uploading the data in a data analyzer 70 via the Internet 9. The device may receive and display an analysis result from the data analyzer 70. The data uploading device 50 may be realized by a personal computer, a smartphone, a tablet computer, or the like. The data uploading device 50 may have a configuration also serving as the cradle 40.

The data uploading device 50 includes a touch panel 52, a keyboard 54, and a substrate 56. On the substrate 56, a CPU 58, a GPU, an IC memory 60, a near field communication module 64, etc. are mounted. The data uploading device 50 establishes data communication with the electronic apparatus 2 by connection through the USB cable 42 and automatic recognition of another near field communication module existing in the reception range of the near field communication module 64. Then, the device acquires measurement data that has not been acquired from the electronic apparatus 2 and saves the data, and transmits the data to the data analyzer 70. Then, the device may receive an analysis result from the data analyzer 70 and display it on the touch panel 52. Note that a device serving as both the data uploading device 50 and the data analyzer 70 may be employed.

Figure 3A:
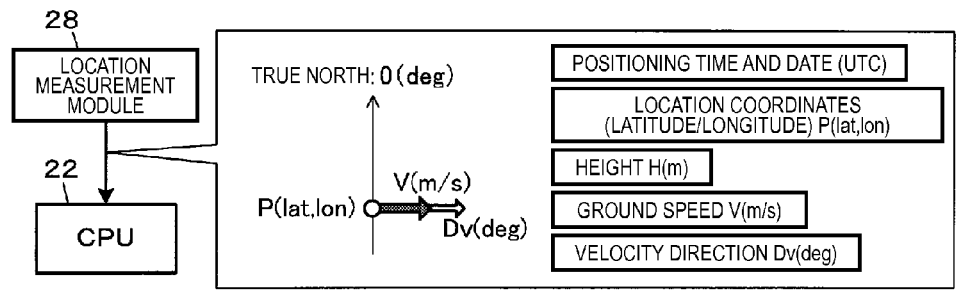
FIGS. 3A to 3C are diagrams for explanation of generation of measurement data in the wearable electronic apparatus.
Figure 3B:
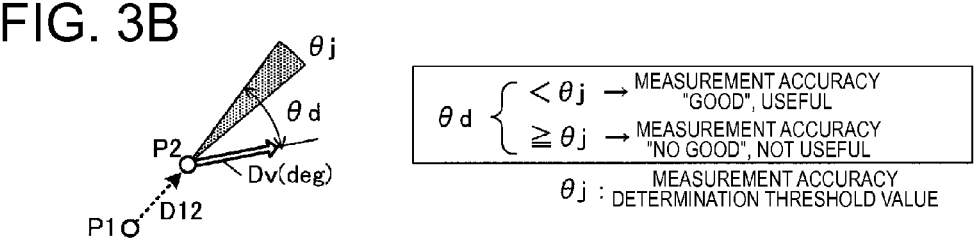
Figure 3C:
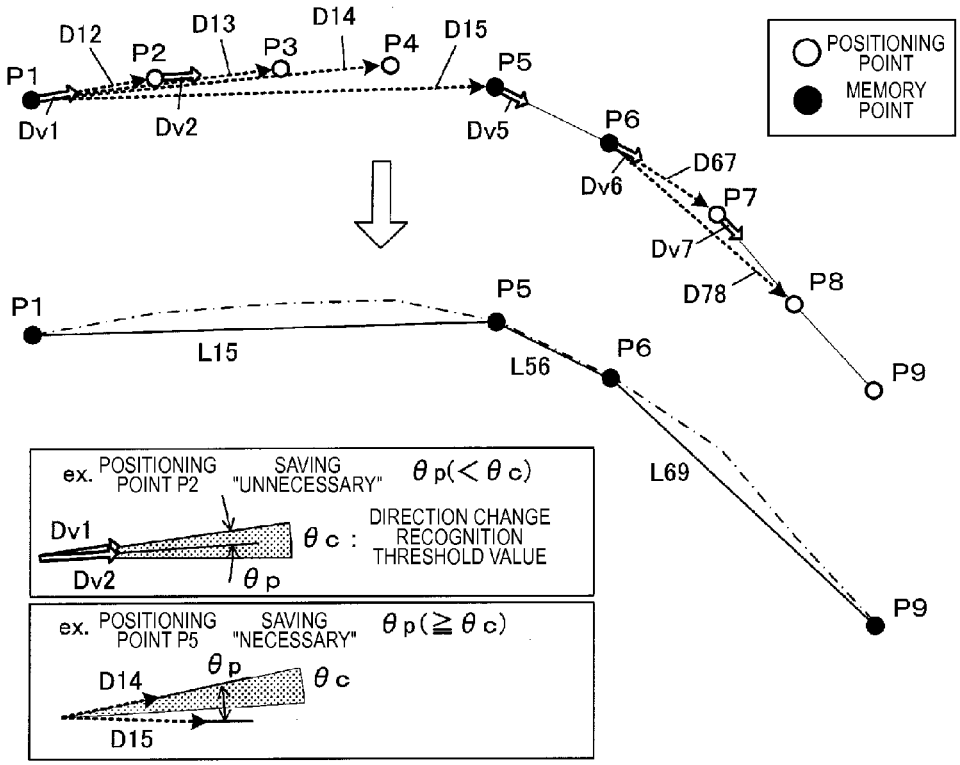

FIGS. 3A to 3C are diagrams for explanation of generation of measurement data in the electronic apparatus 2 of the embodiment.

First, reviewing the method of storing measurement data in the running watch of related art, in related art, all of the location measurement information output from the location measurement module 28 has been stored without change as the measurement data. The location measurement module 28 outputs the location measurement information with a predetermined period. Therefore, in the case of running along a course of about 5 km, for example, the number of memory points reaches 1700 (depending on the pace). In the case of the longer course (e.g., marathon course), the number of memory points further increases and the necessary memory area becomes huge. Further, the rewritable nonvolatile memory (mostly, the flash memory) is used for the memory medium for storing the measurement data not to cause data loss due to running out of the battery, and the nonvolatile memory requires more power for rewriting of data than a volatile RAM. As the number of memory points is larger, the power used for storage is naturally greater in proportion. In view of the requirement of reduction in size and weight, the capacity of the flash memory and the capacity of the battery to be mounted are limited, and, as a result, it may be impossible for the running watch of related art to store all measurement data in the case of the longer course.

Accordingly, in the electronic apparatus 2 of the embodiment, not all of the location measurement information output with the predetermined period from the location measurement module 28 is saved without change, but whether or not newly output location measurement information is useful for data analysis is determined and the useful location measurement information is selectively stored and saved, and thereby, the volume of measurement data in a series of measurement (e.g., single running) is reduced. The volume of measurement data is reduced, thereby, the number of writings in the measurement data memory 26 is reduced, and, as a result, the power consumption may be suppressed and the duration may be extended even with a battery having the same capacity.

The determination of usefulness of the location measurement information in the embodiment includes a first determination in view of measurement accuracy and a second determination depending on the presence or absence of the significant direction change at the positioning point shown by location measurement information at this time. Further, the location measurement information is not stored or saved until the measurement accuracy "good" is determined in the first determination and the direction change is determined in the second determination. That is, the positioning point shown by the location measurement information is registered as "memory point" in the measurement data.

The first determination in view of measurement accuracy is realized to determine whether or not "velocity direction" as the travel direction measured in the latest measurement period and "location direction" as a travel direction obtained based on the traveling of the location of the positioning point satisfy a predetermined approximate condition.

Specifically, as shown in FIG. 3A, the location measurement information includes the positioning time and date (UTC), the location coordinates (latitude/longitude), a height H (m), the ground speed V (m/s: scalar quantity), and the velocity direction Dv (deg: read as travel direction). These values have errors depending on the radio reception environment. It is known that, when the radio reception environment is not good, even if the electronic apparatus 2 (location measurement module 28) travels in a straight line, the positioning point shown by the location measurement information may fluctuate to right and left with respect to the original straight trajectory or, sometimes may cause "measurement jump" deviating from it. Accordingly, in the embodiment, as shown in FIG. 3B, if direction difference θd between location direction D12 from positioning point P1 shown by the location measurement information obtained in the previous measurement period toward positioning point P2 shown by the location measurement information obtained at this time and velocity direction Dv (deg) at this time is equal to or more than measurement accuracy determination threshold value θj (deg), the measurement accuracy "no good" is judged. Conversely, the difference is less than the measurement accuracy determination threshold value θj, the measurement accuracy "good" is judged.

Note that the location coordinates are computed from the location of the GPS satellite and the pseudo-distance, and the ground speed V and the velocity direction Dv are computed based on Doppler as a change in relative position between the GPS satellite and the electronic apparatus 2. The values used for the computations are different, and thus, the location direction and the velocity direction Dv are comparable.

The second determination depending on the presence or absence of the significant direction change is applied if the measurement accuracy "good" is determined in the first determination.

Specifically, for example, as shown in FIG. 3C, (a) direction difference θp between "previous location direction" from the most recent memory point toward the previous positioning point to the latest positioning point and "current location direction" from the most recent memory point toward the latest positioning point is obtained. Alternatively, (b) direction difference θp between "current velocity direction" as the latest velocity direction and "previous velocity direction" as the previous velocity direction is obtained.

Then, the direction difference θp is compared with a direction change recognition threshold value θc. The direction change recognition threshold value θc is a direction change condition showing that the travel direction has changed in the embodiment. If the direction difference θp is less than the predetermined direction change recognition threshold value θc, it is regarded that there has been no significant change in travel direction. As a result, there is no usefulness in storage of the location measurement information, and saving "unnecessary" is determined. Conversely, if the direction difference θp is equal to or more than the predetermined direction change recognition threshold value θc, the positioning location shown by the latest location measurement information may be judged as a key point of direction change, and determined to have usefulness. That is, saving "necessary" is determined and the positioning point shown by the location measurement information is registered as "memory point" in the measurement data.

Specifically, suppose that positioning points P1 to P9 are obtained in the temporal sequence and all of them are determined as measurement "good" in the first determination.

The positioning point P1 shown by the location measurement information obtained in the first measurement period is registered and saved without any condition because the point corresponds to the start point, i.e., as the first memory point. In consideration of the positioning point P2 shown by the location measurement information obtained in the second measurement period, the positioning point P1 in the previous measurement period is the most recent memory point and the only one previous measurement point, and thus, "previous location direction" is not obtained. Therefore, the direction difference θp is obtained from "previous velocity direction Dv1" at the positioning point P1 and "current velocity direction Dv2" at the positioning point P2. Then, the direction difference θp at the positioning point P2 is less than the predetermined direction change recognition threshold value θc, and thereby, it is regarded that there is no significant change in the travel direction and saving "unnecessary" is determined. Therefore, the location measurement information at the positioning point P2 is not registered in the measurement data.

Then, in consideration of the positioning point P3 shown by the location measurement information obtained in the third measurement period, the direction difference θp between previous location direction D12 (positioning point P1 as most recent memory point positioning point P2) and current location direction D13 (positioning point P1 as most recent memory point→positioning point P3) is less than the predetermined direction change recognition threshold value θc, and thereby, the location measurement information of the positioning point P3 is also determined as saving "unnecessary" and not registered in the measurement data like that at the positioning point P2.

In consideration of the positioning point P5 shown by the location measurement information obtained in the fifth measurement period, the direction difference θp between previous location direction D14 (positioning point P1→positioning point P4) and current location direction D15 (positioning point P1→positioning point P5) reaches the predetermined direction change recognition threshold value θc. Thus, the positioning point P5 may be regarded as a key point of direction change and determined as saving "necessary", and the location measurement information at the positioning point P5 is registered and saved in the measurement data memory 26 as part of the measurement data. Thereby, the positioning point P5 is the second "memory point".

Regarding the positioning point P6 in the sixth measurement period, "previous location direction" is not obtained because the positioning point P5 in the previous measurement period is the most recent memory point. Accordingly, the direction difference θp between "previous velocity direction Dv5" at the positioning point P5 and "current velocity direction Dv6" is compared with the direction change recognition threshold value θc. The direction difference θp at the positioning point P5 reaches the direction change recognition threshold value θc. Therefore, saving "necessary" is determined and the positioning point P6 is registered as the third "memory point". Regarding the positioning point P7 in the seventh measurement period, the positioning point P6 in the previous measurement period is the most recent memory point, and the direction difference θp between "previous velocity direction Dv6" at the positioning point P6 and "current velocity direction Dv7" at the positioning point P7 is compared with the direction change recognition threshold value θc. The direction difference θp at the positioning point P7 has not reached the direction change recognition threshold value θc, and saving "unnecessary" is determined. Thus, the location measurement information at the positioning point P7 is not registered in the measurement data.

Regarding the positioning point P8 in the subsequent eighth measurement period, the direction difference θp between current travel direction D78 (positioning point P8 as most recent memory point positioning point P8) and previous travel direction D67 (positioning point P6 as most recent memory point positioning point P7) is less than the direction change recognition threshold value θc and saving "unnecessary" is determined. Thus, the location measurement information at the positioning point P8 is not registered in the measurement data. The positioning point P9 is the measurement point shown by the location measurement information obtained in the measurement period immediately after detection of measurement end operation. That is, the point corresponds to the goal and is automatically registered and saved in the measurement data.

As a result, of the nine positioning points P1 to P9, only four positioning points P1, P5, P6, P9 are registered as "memory points" in the measurement data. In this manner, in the embodiment, thinning of the location measurement information regarded with the lower measurement accuracy, selection of the location measurement information useful for data analysis, thinning of the omissible location measurement information are performed, and thereby, the capacity of the measurement data may be significantly reduced compared to that in the system of related art. Thus, the number of writings in the memory is also reduced. When the number of the writings in the memory is reduced, the power consumption taken for writings is naturally suppressed. If the electronic apparatus 2 has the same memory capacity as that of a similar product in related art realizing reduction in size and weight, the battery lasts longer than that in the related art and more measurement data can be stored than that in the related art.

FIGS. 4A to 4E are diagrams for explanation of a method of computing accumulated travel distances in the embodiment. The locations of the positioning points and the relationships with the points to be the memory points among them are the same as those in the example of FIGS. 3A to 3C.

The electronic apparatus 2 of the embodiment may display a total of the travel distances from the measurement start location to the current location as "accumulated travel distance" on the touch panel 12 (see the accumulated travel distance display 6 in FIG. 1). In the embodiment, the accumulated travel distance is basically obtained as accumulation of the distances between the memory points, i.e., "accumulated distance between memory points", and, in a period until a new memory point is registered, a value obtained by addition of "distance between positioning points" from the most recent memory point to the latest positioning point to "accumulated distance between memory points" is used as temporary "accumulated travel distance".

Figure 4A:
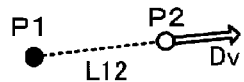
FIGS. 4A to 4E are diagrams for explanation of a method of computing accumulated travel distances.
Figure 4B:
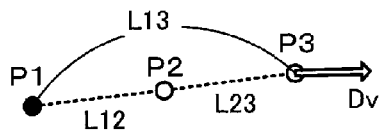
Figure 4C:
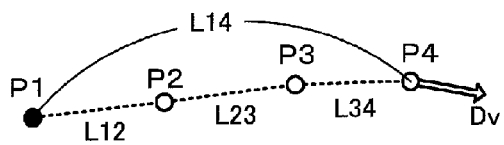

FIG. 4A shows a state in which the positioning point P1 immediately after the start of measurement is registered as the first memory point, and then, the positioning point P2 is obtained in the next measurement period. At this time, there is the only one memory point, and the accumulated memory point distance is "0". Accordingly, distance between positioning points L12 from the positioning point P1 as the most recent memory point to the positioning point P2 is a value of accumulated travel distance LA. In the next measurement period, as shown in FIG. 4B, the positioning point P3 is obtained. The accumulated memory point distance remains "0", and distance between positioning points L13 from the positioning point P1 as the most recent memory point to the positioning point P3 is a value of the accumulated travel distance LA. Similarly, further, in the next measurement period, as shown in FIG. 4C, the positioning point P4 is obtained and the accumulated memory point distance remains "0" at this time, and distance between positioning points L14 from the positioning point P1 to the positioning point P4 is a value of the accumulated travel distance LA.

Figure 4D:
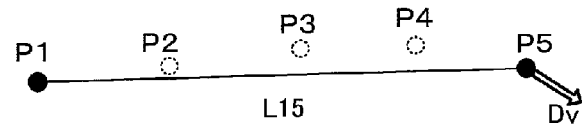
Figure 4E:
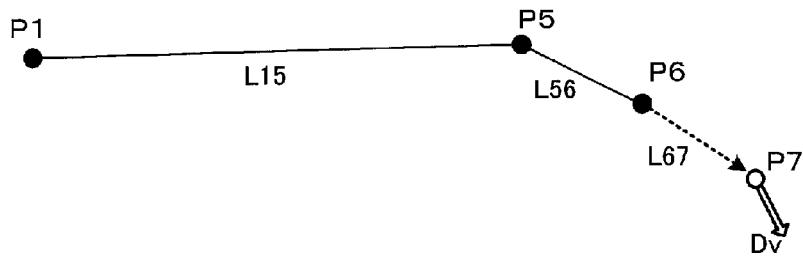

Furthermore, in the period after next, as shown in FIG. 4D, the positioning point P5 is obtained. The positioning point P5 becomes the second memory point. Here, for the first time, accumulated distance between memory points L15 of the memory points P1 to P5 is obtained and used as the accumulated travel distance LA at this time. Then, as shown in FIG. 4E, when the positioning point P6 is obtained, the positioning point is registered as the third memory point and the accumulated distance between memory points is "L15+L56" and this is used as the accumulated travel distance LA at the time when the positioning point P6 is obtained. In addition, when the positioning point P7 is obtained in the next measurement period, the accumulated distance between memory points is "L15+L56", and distance between positioning points L67 from the positioning point P6 as the most recent memory point to the latest positioning point P7 is added thereto and used as the accumulated travel distance LA. That is, the accumulated travel distance LA at the time is "L15+L56+L67".

Subsequently, the accumulated travel distance LA is computed in the same manner. In the example of the positioning points P1 to P9 shown in FIGS. 3A to 3C, the memory points are finally the four points of the positioning points P1, P5, P6, P9, and the accumulated travel distance LA is "L15+L56+L67".

Note that, if the measurement accuracy of the newly obtained location measurement information is "no good", the estimated travel distance for one period may be computed from the ground speed at the positioning point and substituted for a provisional value of the distance between positioning points. In the embodiment, one period is set to one second and the unit of the ground speed V is (m/s), and thus, the ground speed V may be used to correspond to the distance between positioning points without change.

As in the related art, when all of the periodically obtained location measurement information is stored as memory points and the accumulated travel distance LA is computed as accumulation of the distances between memory points, if the radio reception environment is not good as described above, even in the case of linear movement, the positioning point may fluctuate to right and left with respect to the straight movement direction shown by the location measurement information. The accumulated travel distance LA in this case includes an extra distance due to "fluctuations to right and left of positioning point" (in the example of FIG. 3C, the difference between the length of the dashed-dotted line and the length of the straight lines connecting the memory points P1→P5→P6→P9). However, as in the embodiment, the location measurement information of the positioning points in the periods in which the traveling is substantially regarded as the linear movement is thinned, and thereby, the excess distance may be removed from the computation of the accumulated travel distance LA. Accordingly, the more accurate distance than that in the method of computing the accumulated travel distance by simple accumulation of the distances between positioning points may be computed. In other words, a filter effect that removes the positioning error by thinning of the positioning points may be obtained.

Figure 5:
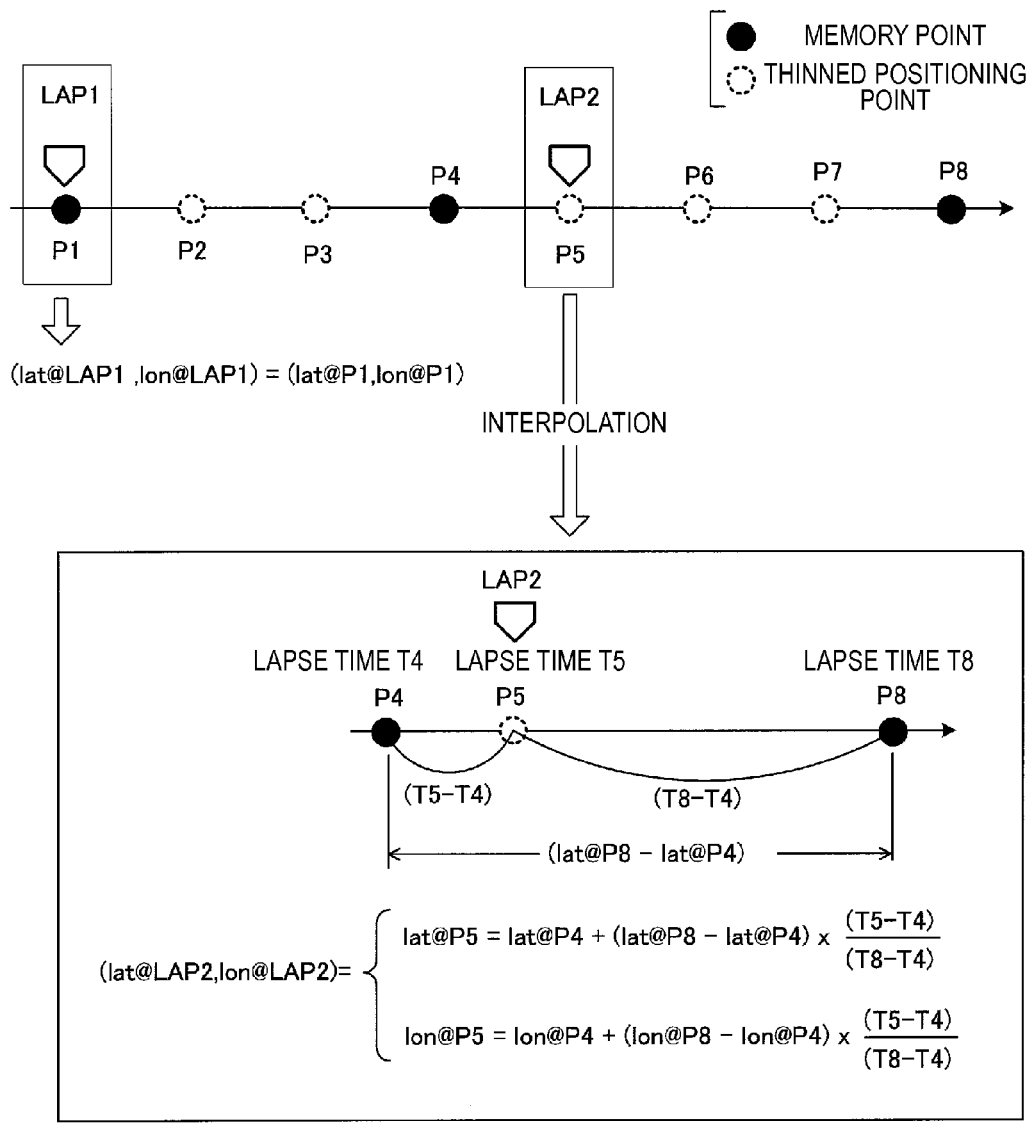
FIG. 5 is a diagram for explanation of a method of determining section measurement points.

FIG. 5 is a diagram for explanation of a method of determining section measurement points in the embodiment. Suppose that positioning points P1 to P8 are obtained in the temporal sequence and the positioning points P1, P4, P8 of them are set as memory points.

The section measurement points (spots where sections end, referred to as "lap spots" hereinafter) are positioning points at which satisfaction of a predetermined lap condition is judged. The lap condition of the embodiment is that, at each time when the section distance reaches 1 km, i.e., the next positioning point at which the accumulated travel distance LA increases by 1 km or more from the previous section measurement point is stored as a lap spot and the time taken for the traveling of the section distance is added to the measurement data as section time information (so-called lap time) and saved.

As the first lap spot LAP1, in the case where the positioning point P1 at the time when the satisfaction of the lap condition is determined is the memory point, the positioning point P1 is stored as the location information (latitude/longitude) of the lap spot, and the positioning point is stored.

On the other hand, in the embodiment, the positioning points may be thinned. In the example of FIG. 5, regarding the lap spot LAP2, the positioning point P5 that is supposed to coincide is thinned. Accordingly, in the embodiment, the location information of the lap spot LAP2 is replaced by dummy data that means "undetermined" and once added to the measurement data. Then, the location information of the lap spot LAP2 replaced by the dummy data at the data analysis is interpolated from the location measurement information of the memory points P4, P8 at the sequential times and dates and used for an analysis. Therefore, even when thinning of the positioning points is performed, the section measurement may be accurately performed.

Next, the data analysis in the embodiment will be explained.

The data measured and stored in the electronic apparatus 2 is output to the data analyzer 70 via the data uploading device 50 and stored and saved. The measurement data includes unique identification information and measurement time and date, and thus, the measurement data once saved in the data analyzer 70 may be retroactively accessed at any time.

Figure 6:
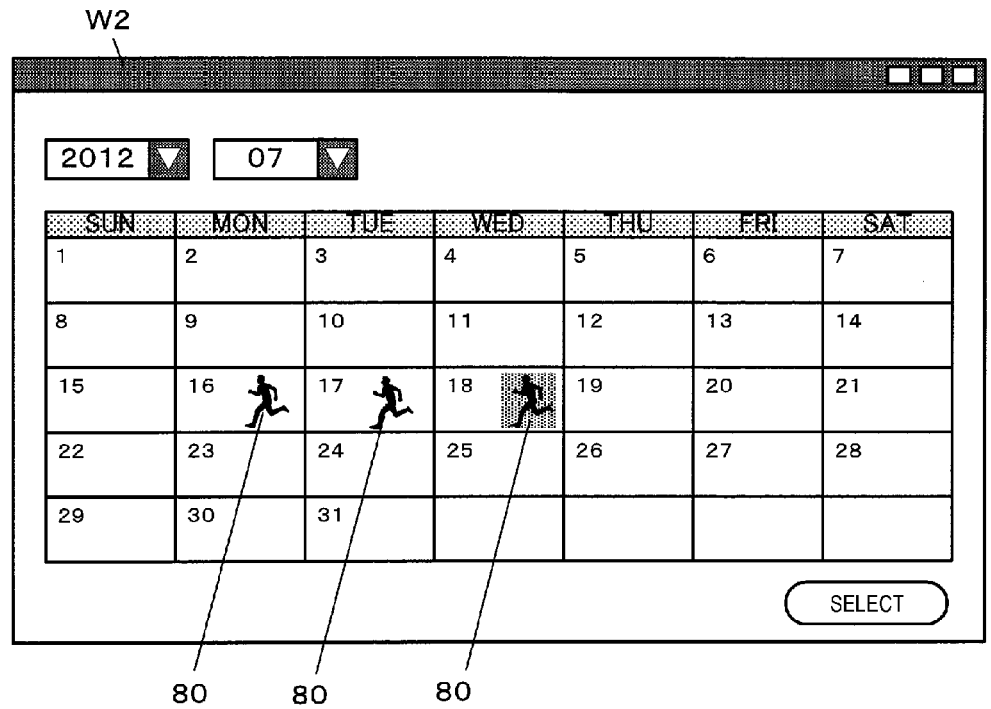
FIG. 6 shows an example of a list display window in calendar form.

For example, the data analyzer 70 may show to the user that the measurement data measured on the day is saved and selectable as an object to be analyzed by placing marks 80 or the like in a list display window in calendar form W2 as shown in FIG. 6. In the list display window in calendar form W2, the mark 80 of the measurement data that the user desires to analyze may be selected. Then, if the user performs a selection determination operation, a graphical display window and a map display window based on the selected measurement data to be analyzed are newly displayed on the touch panel 52.

Figure 7:
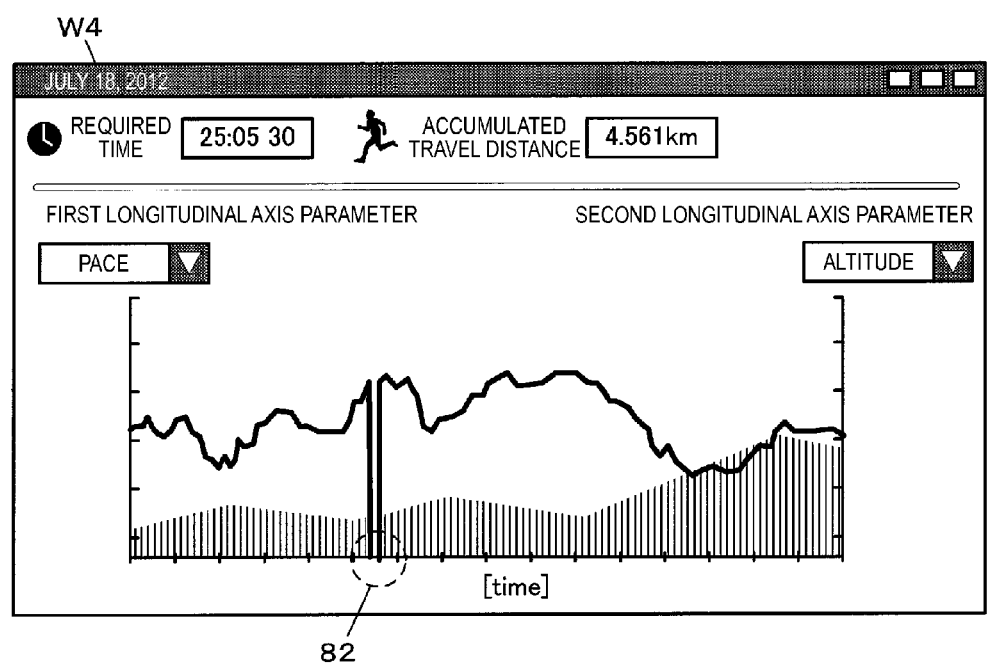
FIG. 7 shows an example of a graphical display window.

FIG. 7 shows an example of the graphical display window. In a graphical display window W4 of the embodiment, a graph is displayed with required time and accumulated travel distance of running. The graph of the embodiment has a first longitudinal axis (left longitudinal axis) and a second longitudinal axis (right longitudinal axis) with a lateral axis in common. The lateral axis is fixed to lapse time. The parameters of the first longitudinal axis and the second longitudinal axis may be changed by the user. In the example of FIG. 7, the first longitudinal axis is set to "pace" and the second longitudinal axis is set to "altitude", respectively, and other selectable parameters including pitch, average calorie consumption, and stride may be appropriately set, for example. Further, the scale of the longitudinal axis is automatically adjusted. In this regard, regarding values having a certain level of larger differences from the average value or median value, their scales are not automatically adjusted. In the example of FIG. 7, there is data with extremely lower numeric values than those of other data (data near sign 82) on "pace" of the first longitudinal axis. The example of FIG. 7 is data of a spot on which the user had to stop temporarily for traffic signals and avoidance of danger during running. In the scaling of the first longitudinal axis, the data with extremely lower (or higher) numeric values is not included for the scaling automatic adjustment, and the data is out of the range of graphic display.

Figure 8:
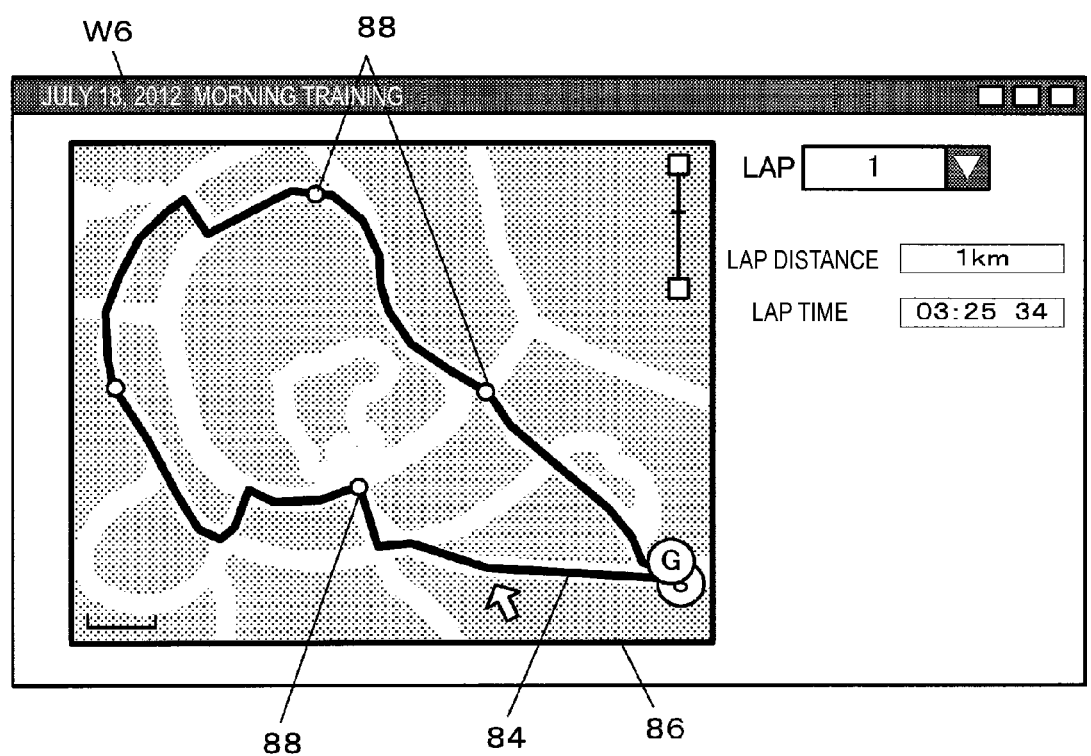
FIG. 8 shows an example of a map display window.

FIG. 8 shows an example of the map display window. In a map display window W6 of the embodiment, a trajectory 84 of running is drawn on a map 86, and section measurement points 88 are displayed on the trajectory 84. In the case where a trajectory is displayed to connect all of the location measurement information obtained from the location measurement module 28 as in related art, the trajectory is disturbed into a zigzag form due to the fluctuations of the location measurement information to right and left and the measurement jump. However, only the positioning points changed in direction are selected as the memory points as in the embodiment, and thereby, an orderly and accurate trajectory without minute fluctuations to right and left that is unwanted and undesirable in view may be displayed.

Next, a functional configuration of the embodiment will be explained.

Figure 9:
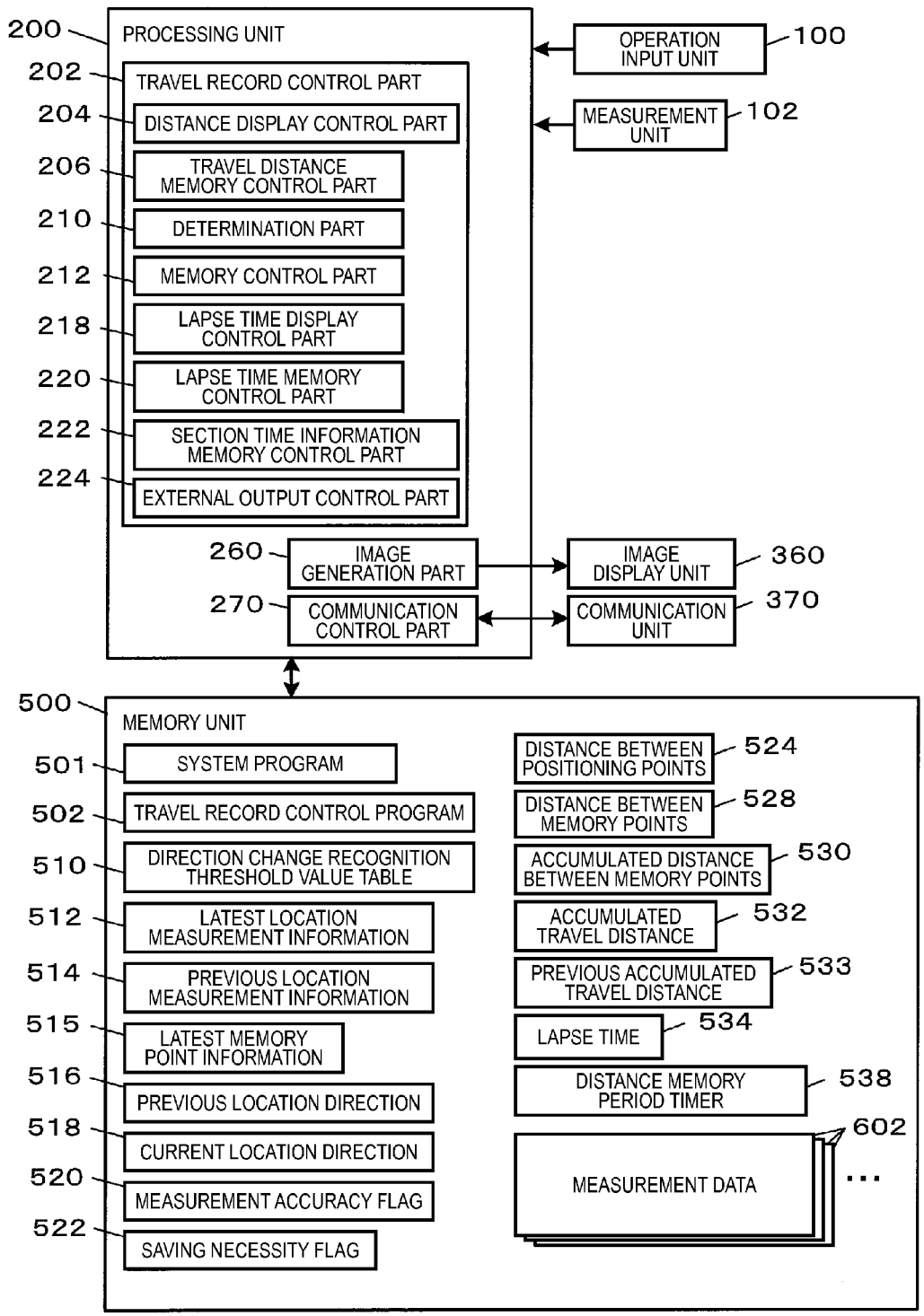
FIG. 9 shows a configuration example of functional blocks of the wearable electronic apparatus.

FIG. 9 is a functional block diagram showing a functional configuration example in the embodiment.

The electronic apparatus 2 includes an operation input unit 100, a measurement unit 102, a processing unit 200, an image display unit 360, a communication unit 370, and a memory unit 500.

The operation input unit 100 outputs operation input signals in response to various operation inputs performed by the user to the processing unit 200. For example, the unit may be realized not only by devices that the user directly operates with fingers and hands including a button switch and a touch panel but also devices that sense a motion and a posture including an accelerator sensor, an angular velocity sensor, a tilt sensor, and a geomagnetic sensor. The touch panel 12 and the operation switches 16 in FIG. 1 correspond to the unit.

The measurement unit 102 measures the location with a predetermined period. Specifically, the unit receives signals from the location measurement system, computes location measurement information based on the signals received with the predetermined period, and outputs the information to the processing unit 200. The location measurement module 28 in FIG. 1 corresponds to the unit.

The processing unit 200 is realized by a micro processor including a CPU and a GPU and a component element including an IC memory, and performs input/output control of data between the respective functional units of the apparatus including the operation input unit 100 and the memory unit 500. Further, the unit executes various operation processing based on predetermined programs, data, or the like to control the operation of the electronic apparatus 2. In FIG. 1, the substrate 20 corresponds to the unit.

Furthermore, the processing unit 200 of the embodiment includes a travel record control part 202, an image generation part 260, and a communication control part 270.

The travel record control part 202 executes integrative measurement control, computation processing of measurement result, and various operation processing relating to storage and saving. The travel record control part 202 of the embodiment includes a distance display control part 204, a travel distance memory control part 206, a determination part 210, a memory control part 212, a lapse time display control part 218, a lapse time memory control part 220, a section time information memory control part 222, and an external output control part 224.

The distance display control part 204 computes the accumulated travel distance LA based on the measurement results in the measurement unit 102 to perform display control.

The travel distance memory control part 206 performs control of allowing the memory unit 500 to store the accumulated travel distance LA computed by the distance display control part 204 with respect to each of distance memory periods (e.g., every six seconds) at the longer intervals than the measurement period with which the measurement unit 102 computes and outputs positioning information. Thereby, the accumulated travel distance LA computed with the distance memory period is stored and saved in the measurement data 602 of the memory unit 500.

The determination part 210 refers to the measurement results in the past at each time when the measurement is performed in the measurement unit 102, i.e., at each time when the location measurement information is computed, and determines whether or not the measurement result is saved. The location measurement information determined as saving "necessary" is stored and saved as the measurement data 602 of the memory unit 500.

Specifically, as the first determination, if the movement direction measured by the measurement unit 102 (the velocity direction Dv in FIG. 3B) and the travel direction based on the locations measured by the measurement unit 102 (the location direction D12 in FIG. 3B) do not satisfy a predetermined approximate condition (the direction difference θd in FIG. 3B is less than a measurement determination threshold value θj, the determination part 210 of the embodiment determines that the measurement result is not saved.

Further, as the second determination, if a direction change condition showing that the movement direction has been changed based on the measurement result of the measurement unit 102 is satisfied, the part determines that the measurement result is saved. The direction change condition in the embodiment is that (a) the direction difference θp between "previous location direction" from the most recent memory point toward the previous positioning point to the latest measurement point and "current location direction" from the most recent memory point toward the latest measurement point or (b) the direction difference θp between "current velocity direction" as the latest velocity direction and "previous velocity direction" as the previous velocity direction is equal to or more than the direction change recognition threshold value θc (see FIG. 3C).

If the determination part 210 makes a positive determination, the memory control part 212 allows the memory unit 500 to store the measurement result.

The lapse time display control part 218 performs control of computing a lapse time from the start of measurement, i.e., a lapse time from the start of computation of the accumulated travel distance LA and allowing the image display part 360 to display the time.

The lapse time memory control part 220 stores the lapse time in the memory unit 500 in correspondence with the measurement result stored in the memory unit 500. In the embodiment, the ground speed V and the height H at the lapse time computation are associated and stored.

The section time information memory control part 222 performs control of allowing the memory unit 500 to store the section time information (so-called lap time) as the lapse time at each time when the accumulated travel distance LA reaches a predetermined section distance (e.g., 1 km) or the time taken for traveling of the section distance.

The external output control part 224 performs control of outputting data of the measurement results (measurement data 602) etc. stored in the memory unit 500 to an external device. In the embodiment, the measurement data 602 contains the accumulated travel distance LA with respect to each distance memory period, and thus, the external output control part 224 substantially performs control of outputting data of the accumulated travel distance LA stored in the memory unit 500 to the external device. Further, the measurement data 602 contains the data of lapse time and the data of section time information, so that the external output control part 224 may output the data to the external device.

The image generation part 260 is realized by a CPU, a driver IC for a liquid crystal display, a GPU (Graphics Processing Unit), a program including video codec, an IC memory for drawing frame including a frame buffer, an IC memory used for development of texture data, etc. The image generation part 260 performs control of displaying various images on the image display part 360.

The image display part 360 displays various images based on control signals input from the image generation part 260. For example, the part may be realized by an image display device including a flat panel display and a projector. In the embodiment, the touch panel 12 in FIG. 1 corresponds to the part.

The communication control part 270 executes data processing with respect to data communication and realizes exchange of data between the external device and itself via the communication part 370.

The communication part 370 realizes the data communication between the external device and itself. For example, the part is realized by a wireless communication device, a jack of a communication cable for wired communication, a control circuit, or the like, and the near field communication module 30 in FIG. 1 corresponds to the part.

The memory unit 500 stores programs, various initial setting data, etc. for the processing unit 200 to realize various functions for integrative control of the electronic apparatus 2. Further, the unit may be used as a work area of computation processing by the processing unit 200 and may temporarily store computation results from execution by the processing unit 200 according to the various programs, input data input from the operation input unit 100, data of measurement results from measurement in the measurement unit 102, etc. The function is realized by an IC memory including a RAM and a flash memory, for example. In FIG. 1, the main memory 24 and the measurement data memory 26 mounted on the substrate 20 correspond to the unit.

The memory unit 500 of the embodiment stores a system program 501, a travel record control program 502, and a direction change recognition threshold value table 510 in advance.

Further, with the start of measurement, as information stored and rewritten at all times, latest location measurement information 512, previous location measurement information 514, latest memory point information 515, a previous location direction 516, a current location direction 518, a measurement accuracy flag 520, a saving necessity flag 522, a distance between positioning points 524, a distance between memory points 528, an accumulated distance between memory points 530, an accumulated travel distance 532, a previous accumulated travel distance 533, a lapse time 534, a distance memory period timer 538, and measurement data 602 are stored. In addition, a timing timer, a flag, etc. may be appropriately stored.

The system program 501 is a program for the electronic apparatus 2 to realize a basic function as a computer. The travel record control program 502 is application software for realization of the function as the travel record control part 202 when read out and executed by the processing unit 200, however, the program may be incorporated as a part of the system program 501. The direction change recognition threshold value table 510 associates and stores the sections of the ground speed V and the direction change recognition threshold values θc corresponding to the respective sections.

The latest location measurement information 512 is the newest location measurement information. The previous location measurement information 514 stores the location measurement information obtained in the previous measurement period. The latest memory point information 515 stores the location measurement information of the positioning point most recently set to the memory point, i.e., the most recent memory point.

The previous location direction 516 stores the direction from the most recent memory point toward the positioning point of the previous measurement period. The current location direction 518 stores the direction from the most recent memory point toward the latest positioning point shown by the latest location measurement information 512.

The measurement accuracy flag 520 is a flag indicating "good"/"no good" of the measurement accuracy of the latest location measurement information. The saving necessity flag 522 is a flag indicating whether or not the latest location measurement information is stored and saved in the measurement data 602.

The distance between positioning points 524 stores a distance computed based on the location coordinates from the most recent memory point to the latest positioning point shown by the latest location measurement information 512. The distance between memory points 528 stores a distance computed based on the location coordinates from the most recent memory point to the positioning point determined as saving "necessary", i.e., a new memory point.

The accumulated distance between memory points 530 stores an accumulated value of the distance between memory points 528. The accumulated value corresponds to a distance obtained by sequentially connecting all memory points that have been registered and saved to the latest memory point. The value is reset to "0" in initialization before the start of measurement.

The accumulated travel distance 532 stores the latest accumulated travel distance LA with reference to the start spot of measurement.

The previous accumulated travel distance 533 stores the accumulated travel distance LA previous to the latest value.

The lapse time 534 is reset to "0" in initialization before the start of measurement in which the lapse time with reference to the start time and date of measurement is stored.

The distance memory period timer 538 is a timer for timing the distance memory period.

Figure 10:
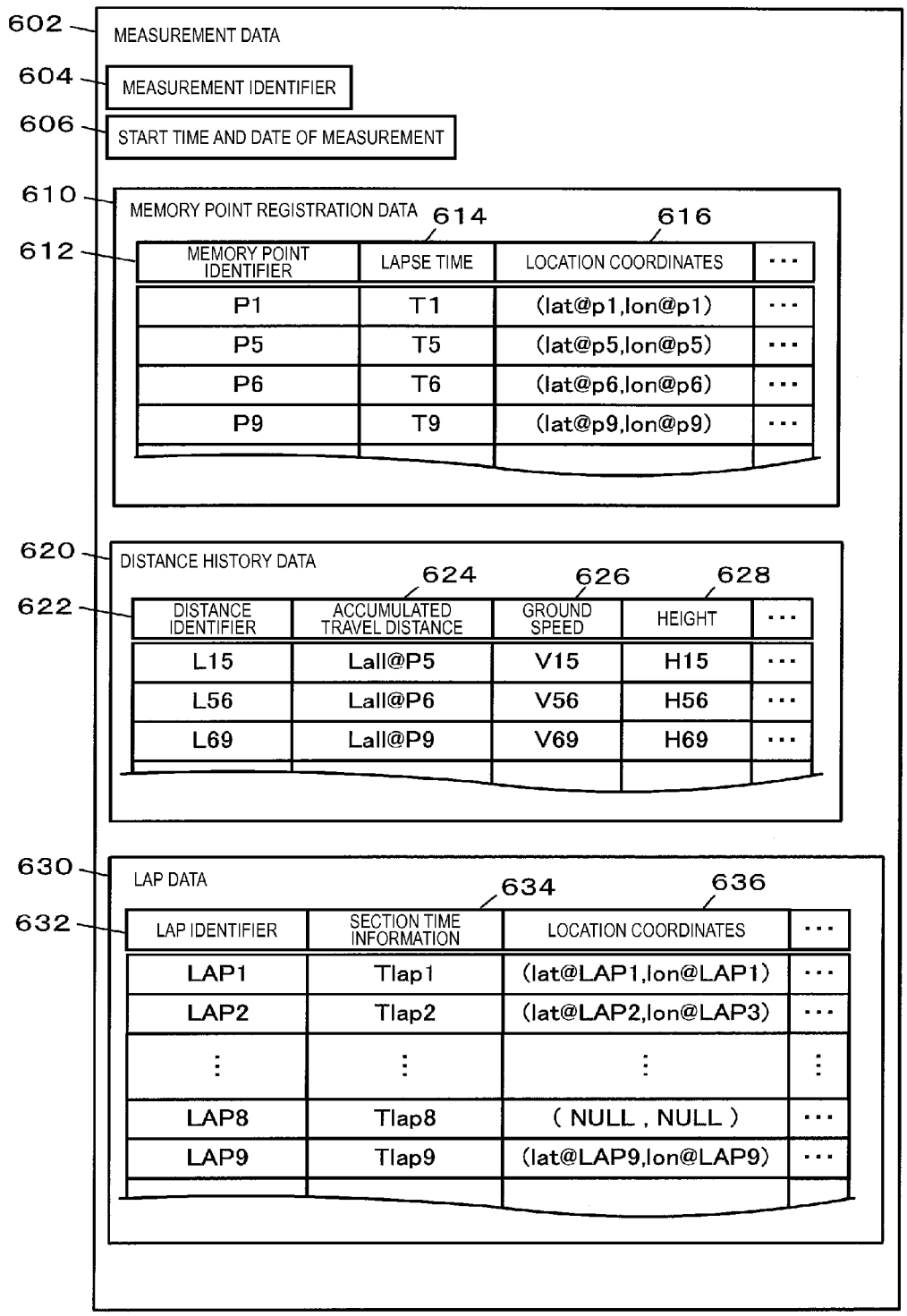
FIG. 10 shows a data configuration example of measurement data.

The measurement data 602 stores data of location measurement information measured from detection of the operation of the start of measurement to detection of the operation of the end of measurement or the like. For example, as shown in FIG. 10, a measurement identifier 604, a start time and date of measurement 606, memory point registration data 610, distance history data 620, and lap data 630 provided at the start of measurement are stored.

The memory point registration data 610 stores location measurement information of the positioning point determined as saving "necessary", i.e. the memory point. In the embodiment, the GPS is used for location measurement, and the memory point registration data 610 corresponds to so-called "GPS log". In the embodiment, with respect to each registration of the memory point, a memory point identifier 612, a lapse time 614 from the start of measurement, location coordinates 616 are associated and stored. Obviously, other information may be associated and stored.

The distance history data 620 stores, in the distance memory period, the history of the accumulated travel distances LA that have been computed at the time when the distance memory period comes. For example, a distance identifier 622, an accumulated travel distance 624 at the time, a ground speed 626, and a height 628 are associated and stored. Obviously, other information may be associated and stored.

The lap data 630 sequentially stores results of section measurement (so-called lap (LAP)). For example, as a result of one section measurement, a lap identifier 632, section time information 634 from the start of measurement, and location coordinates 636 of the section measurement spot are associated and stored. The section time information 634 is, at each time when the accumulated travel distance LA reaches a predetermined section distance (e.g., 1 km), either of the lapse time to reach the section distance or time taken for traveling of the section distance, and the former is used in the embodiment. Obviously, other information may be associated and stored.

Figure 11:
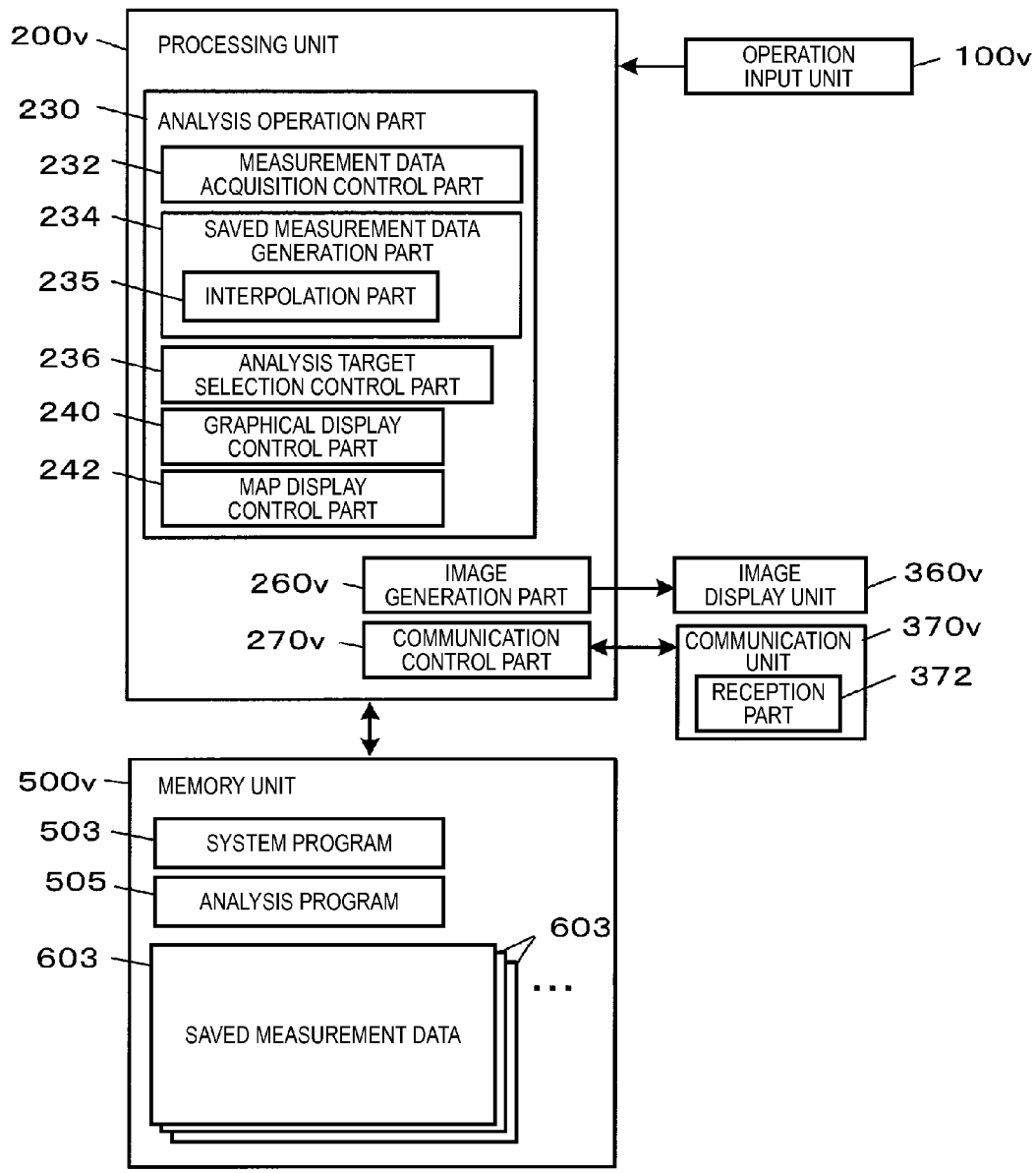
FIG. 11 shows a configuration example of functional blocks of a data analyzer.

FIG. 11 is a functional block diagram showing a functional configuration example of the data analyzer 70 in the embodiment. The data analyzer 70 is a computer including an operation input unit 100v, a processing unit 200v, an image display unit 360v, a communication unit 370v, and a memory unit 500v, the so-called server.

The operation input unit 100v corresponds to a keyboard and a mouse, and corresponds to the operation input unit 100 in the electronic apparatus 2.

The processing unit 200v includes a CPU or the like, and corresponds to the processing unit 200 in the electronic apparatus 2, and performs integrative control of the operation of the data analyzer 70. In the embodiment, the unit includes an analysis operation part 230, an image generation part 260v, and a communication control part 270v. Further, the analysis operation part 230 includes a measurement data acquisition control part 232, a saved measurement data generation part 234, an analysis target selection control part 236, a graphical display control part 240, and a map display control part 242.

The measurement data acquisition control part 232 performs control for acquisition of the measurement data 602 not yet acquired and output from the electronic apparatus 2. In the embodiment, the part performs control for reception and acquisition of the measurement data 602 via a reception part 372 of the communication part 370v (corresponding to the communication part 370 in the electronic apparatus 2) using the communication control part 270v (corresponding to the communication control part 270 in the electronic apparatus 2).

The saved measurement data generation part 234 generates saved measurement data 603 from the acquired measurement data 602, and performs control for storing the data in the memory unit 500v (corresponding to the memory unit 500 in the electronic apparatus 2). Further, the saved measurement data generation part 234 includes an interpolation part 235 that interpolates and replace information showing a target of interpolation contained in the measurement data 602.

In the embodiment, the interpolation part 235 extracts the location coordinates 636 provided with a predetermined value that means "undetermined" ("NULL" in FIG. 10 corresponds to the value) in the lap data 630 of the measurement data 602. Then, the part refers to the memory point registration data 610 and interpolate the location coordinates 616 of the memory points with the sequential section time information 634, and performs processing of obtaining and rewriting the undetermined value. If there is no data of the measurement result corresponding to the section time information 634 in the received measurement data 602, the data may be generated by interpolating the measurement result corresponding to the section time information 634 based on the data of the lapse times before and after the section time information 634 and the data of the measurement results corresponding to the lapse times. Note that the data uploading device 50 may have the function of the interpolation part 235 and the data uploading device 50 interpolates and uploads the measurement data 602 to the data analyzer 70.

Further, the saved measurement data generation part 234 may thin the acquired measurement data 602. In the embodiment, the minimum number of scale marks of the lateral axis of the graph of the graphical display window W4 are fixed, and, if the number of memory points registered in the memory point registration data 610 is larger than the minimum number of scale marks, the memory points may be thinned. Further, if the number of pieces of distance data registered in the distance history data 620 is larger than the minimum number of scale marks, the distance data may be thinned. Thinning may be appropriately set such that, not only one of a plurality of pieces of sequential data in the temporal sequence is simply deleted but also the plurality of pieces of data are replaced by average values thereof.

The analysis target selection control part 236 performs control of allowing the user to select one of the saved measurement data 603 as a target of data analysis. In the embodiment, the part generates data for displaying the list display window in calendar form W2 on the touch panel 52 of the data uploading device 50.

Both the graphical display control part 240 and the map display control part 242 have part of the function of data analysis. The former performs processing of generating data for displaying the graphical display window W4 on the touch panel 52 of the data uploading device 50, and the latter performs processing of generating data for displaying the map display window W6.

The communication unit 370v corresponds to the communication unit 370 in the electronic apparatus 2. In the embodiment, the unit also serves as the reception part 372 that receives the data output from the electronic apparatus 2.

The memory unit 500v corresponds to the memory unit 500 in the electronic apparatus 2. In the memory unit 500v of the embodiment, a system program 503, an analysis program 505, and the saved measurement data 603 are stored.

The system program 503 is a program for the data analyzer 70 to realize the basic function as the computer. The analysis program 505 is application software for realization of the function as the analysis operation part 230 when readout and executed by the processing unit 200v. The program may be incorporated as a part of the system program 503.

Figure 12:
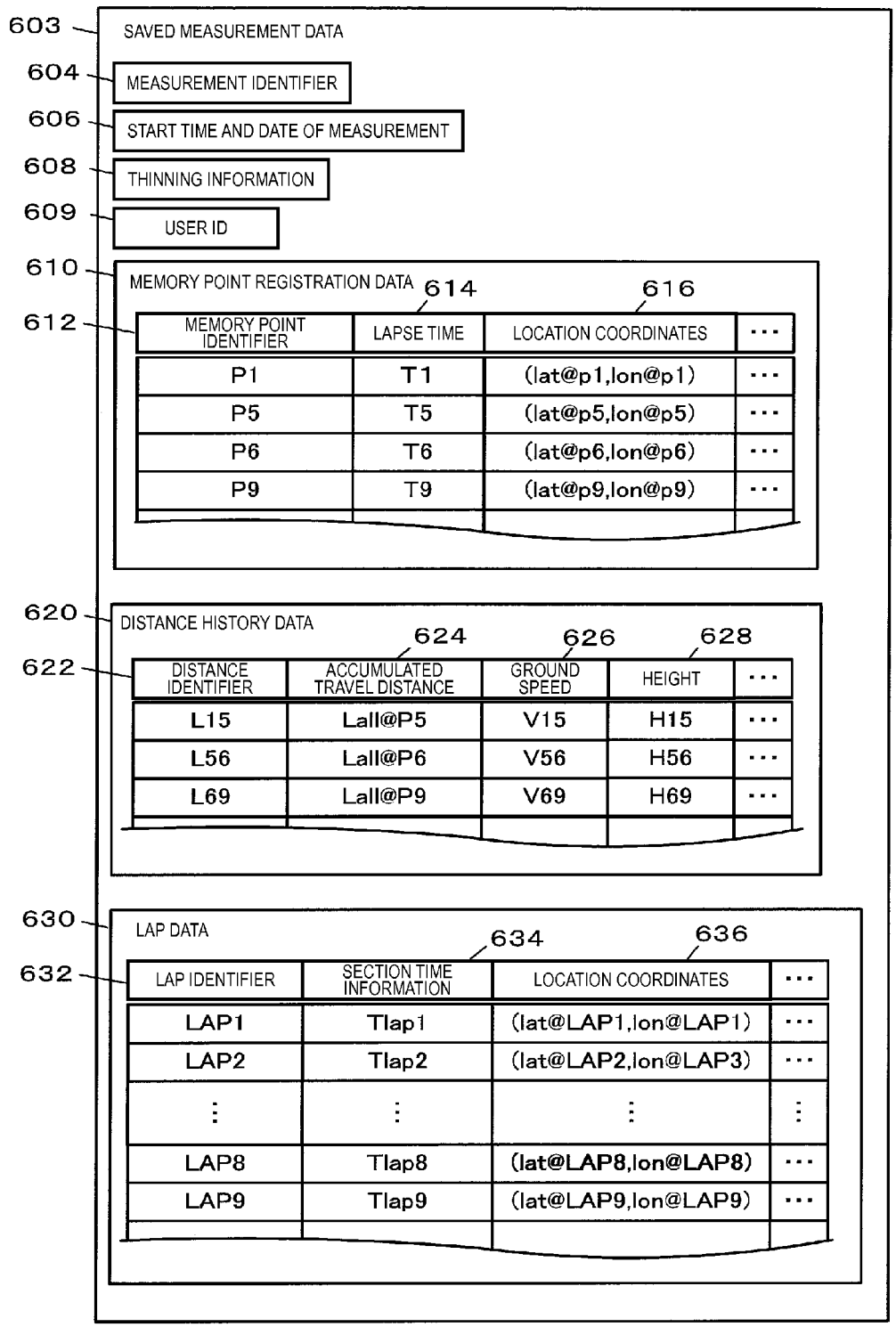
FIG. 12 shows an example of a data configuration of saved measurement data.

The saved measurement data 603 basically has the same data configuration as that of the measurement data 602 as shown in FIG. 12, and includes thinning information 608 and a user ID 609. The thinning information 608 is predetermined information showing thinning of the data of the received measurement data 602 as the original when the saved measurement data 603 is generated. For example, when thinning is performed by simply deleting every other distance history data 620, the distance computation period to be applied to the distance history data 620 after thinning is stored. Further, in the case where two memory points of the memory point registration data 610 are replaced by one new memory point having an average value of them, the number of the original memory points "2" corresponding to the replacement ratio may be stored.

Next, the operation of the electronic apparatus 2 will be explained.

Figure 13:
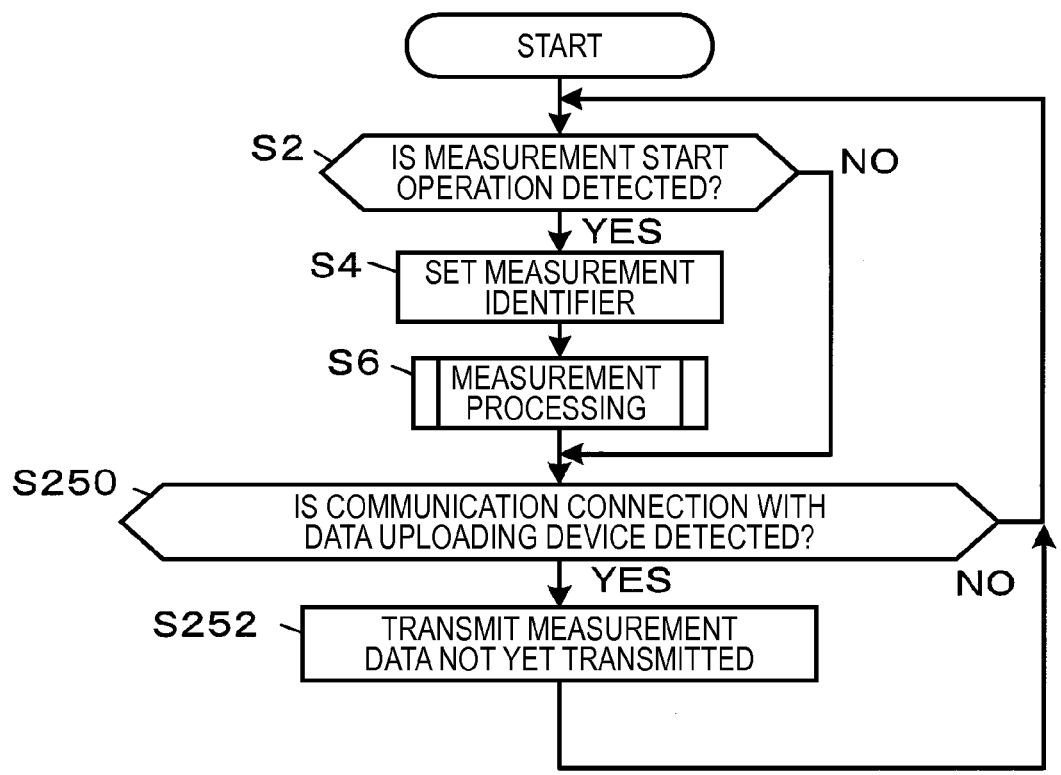
FIG. 13 is a flowchart for explanation of a flow of processing (travel record control processing) in the wearable electronic apparatus.

FIG. 13 is a flowchart for explanation of a flow of processing (travel record control processing) in the electronic apparatus 2 in the embodiment. If detecting a predetermined measurement start operation such as pressing down of the predetermined operation switch 16 (see FIG. 1) (YES at step S2), the processing unit 200 of the electronic apparatus 2 sets the unique measurement identifier (step S4) and executes measurement processing (step S6). That is, the unit starts measurement.

Figure 14:
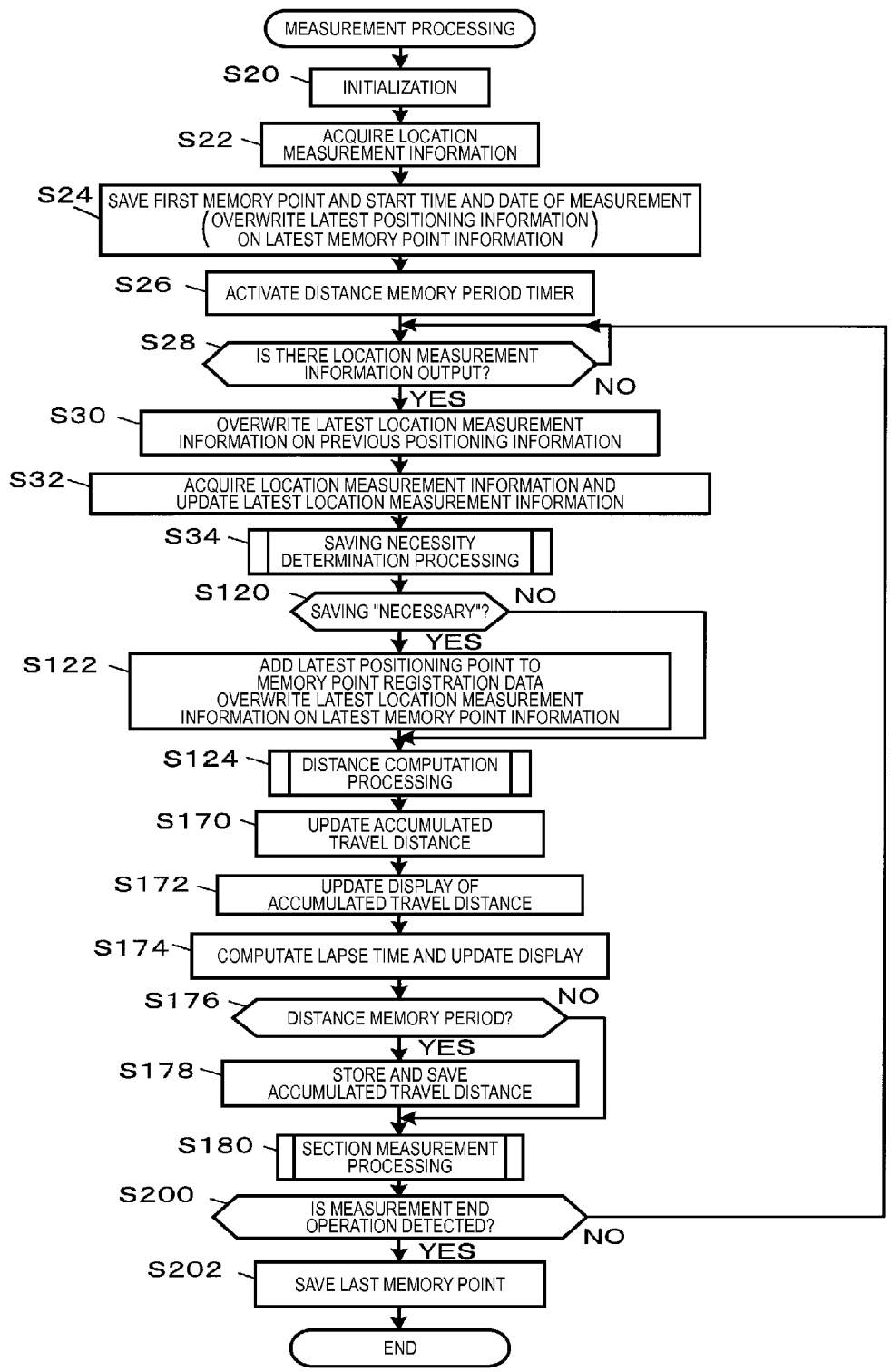
FIG. 14 is a flowchart for explanation of a flow of measurement processing.

FIG. 14 is a flowchart for explanation of a flow of the measurement processing in the embodiment.

In the measurement processing, the processing unit 200 of the electronic apparatus 2 first performs initialization (step S20).

In the initialization, the unit secures the memory area of the measurement data 602 and clears the latest location measurement information 512, the previous location measurement information 514, and the latest memory point information 515. Further, the unit resets the previous location direction 516, the current location direction 518, the distance between positioning points 524, the distance between memory points 528, the accumulated distance between memory points 530, the accumulated travel distance 532, the previous accumulated travel distance 533, the lapse time 534, and the distance memory period timer 538 to "0".

Then, the processing unit 200 acquires the location measurement information from the measurement unit 102 and stores the location measurement information in the latest location measurement information 512 (step S22). Then, the unit additionally registers the first positioning point shown by the location measurement information as the first memory point to the memory point registration data 610 of the measurement data 602, and overwrites the location measurement information on the latest memory point information 515. Further, the unit stores and saves the positioning time and date of the location measurement information as the start time and date of measurement 606 (step S24). Then, the processing unit 200 activates the distance memory period timer 538 (step S26).

Then, if new location measurement information is output from the measurement unit 102 (YES at step S28), the processing unit 200 overwrites the content of the latest location measurement information 512 in the previous location measurement information 514 (step S30), acquires the new location measurement information, and updates the latest location measurement information 512 (step S32). Then, the unit executes saving necessity determination processing to determine whether or not the positioning point shown by the latest location measurement information 512 is registered as a memory point (step S34).

Figure 15:
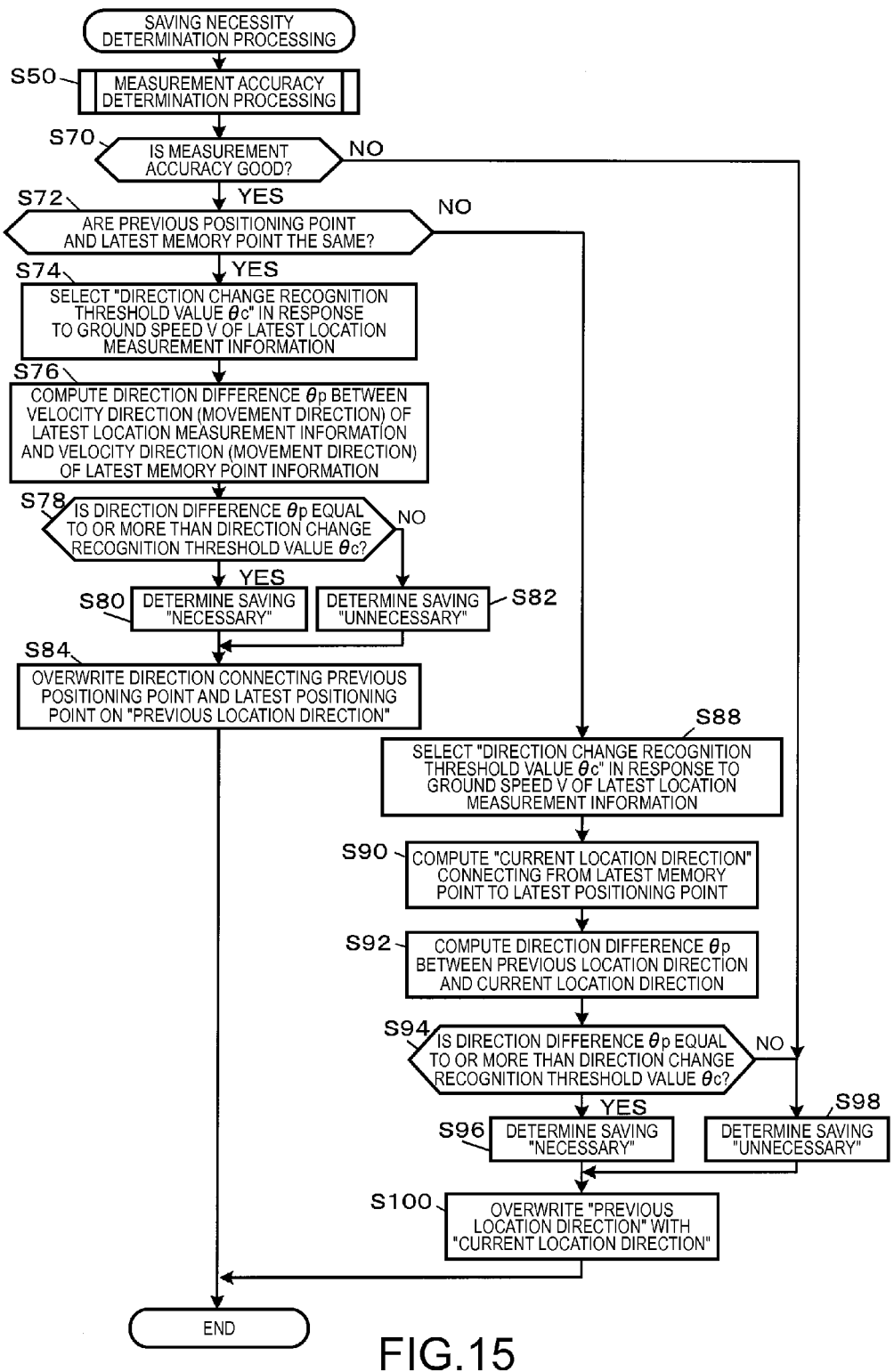
FIG. 15 is a flowchart for explanation of a flow of saving necessity determination processing.

FIG. 15 is a flowchart for explanation of a flow of the saving necessity determination processing in the embodiment. In the processing, the processing unit 200 of the electronic apparatus 2 first executes measurement accuracy determination processing (step S50).

Figure 16:
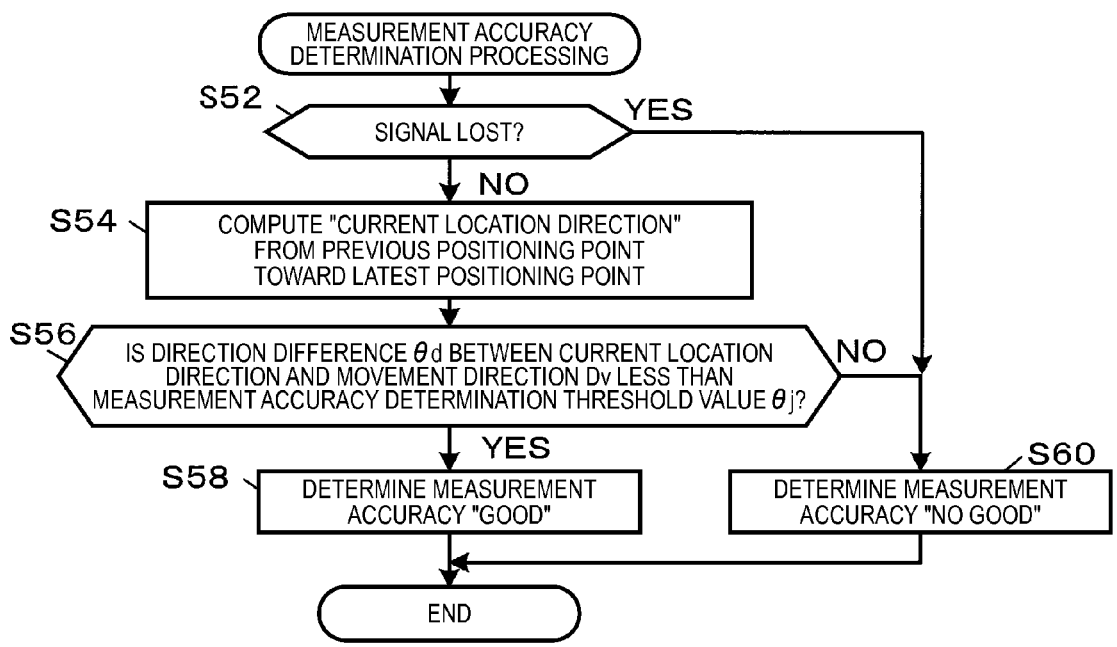
FIG. 16 is a flowchart for explanation of a flow of measurement accuracy determination processing.

FIG. 16 is a flowchart for explanation of a flow of the measurement accuracy determination processing in the embodiment. The measurement accuracy determination processing performs the first determination based on the measurement accuracy with respect to the location measurement information (see FIG. 3B). Specifically, in the processing, if the latest location measurement information 512 is not the value indicating a state in which signal reception from the location measurement system has been impossible, i.e., a signal lost state (NO at step S52), the processing unit 200 first computes a direction from the previous positioning point shown by the previous location measurement information 514 to the latest positioning point shown by the latest location measurement information 512, i.e., the current location direction 518 (step S54).

Then, the unit computes the direction difference θd between the velocity direction Dv (see FIG. 3A) of the latest location measurement information 512 and the current location direction 518 that has been computed, and compares the computed direction difference θd with the predetermined measurement accuracy determination threshold value θj. If the direction difference θd is less than the measurement accuracy determination threshold value θj (YES at step S56), the unit determines the measurement accuracy "good" and sets the measurement accuracy flag 520 to "1 (good)" (step S58), and ends the measurement accuracy determination processing.

Conversely, if the direction difference θd is equal to or more than the measurement accuracy determination threshold value θj (NO at step S56), the processing unit 200 regards the measurement accuracy as "no good" and sets the measurement accuracy flag 520 to "0 (no good)" (step S60), and ends the measurement accuracy determination processing.

Further, in the first place, if the latest location measurement information 512 is a value indicating signal lost (YES at step S52), the processing unit 200 also determines the measurement accuracy "no good" and sets the measurement accuracy flag 520 to "0 (no good)" (step S60), and ends the measurement accuracy determination processing.

Returning to the flowchart in FIG. 15, if the measurement accuracy "good" is determined (YES at step S70) by the measurement accuracy determination processing, the unit determines whether or not the previous positioning point shown by the previous location measurement information 514 and the latest memory point shown by the latest memory point information 515 are the same.

If the previous positioning point and the latest memory point are the same (YES at step S72), the processing unit 200 selects the direction change recognition threshold value θc (see FIG. 3C) in response to the ground speed V contained in the latest location measurement information 512 from the direction change recognition threshold value table 510 (step S74).

Then, the unit computes the direction difference θp between the velocity direction Dv contained in the latest location measurement information 512, i.e., the movement direction and the velocity direction Dv contained in the latest memory point information 515 (step S76), and, if the computed direction difference θp reaches the direction change recognition threshold value θc that has been selected (YES at step S78), the processing unit 200 determines saving "necessary", and sets the saving necessity flag 522 to "1 (necessary)" (step S80). Conversely, if the computed direction difference θp is less than the direction change recognition threshold value θc that has been selected (NO at step S78), the unit determines saving "unnecessary", and sets the saving necessity flag 522 to "0 (unnecessary)" (step S82). Then, the unit overwrites the direction connecting from the previous positioning point shown by the previous location measurement information 514 to the positioning point shown by the latest location measurement information 512 as the previous location direction 516 (step S84), and ends the saving necessity determination processing.

At step S72, if a determination that the previous positioning point and the latest memory point are different is made (NO at step S72), the processing unit 200 selects the direction change recognition threshold value θc (step S88), computes the direction from the previous positioning point toward the latest memory point, and overwrites the direction on the current location direction 518 (step S90). Then, the unit computes the computed direction difference θp between the previous location direction 516 and the current location direction 518 (step S92), and, if the direction difference θp reaches the direction change recognition threshold value θc that has been selected (YES at step S94), the unit determines saving (necessary) (step S96), overwrites the previous location direction 516 with the current location direction 518 (step S100), and ends the saving necessity determination processing. If the direction difference θp does not reach the direction change recognition threshold value θc (NO at step S94), the unit determines saving (unnecessary) (step S98), overwrites the previous location direction 516 with the content of the current location direction 518 (step S100), and ends the saving necessity determination processing.

Further, at step S70, in the first place, if the measurement accuracy "no good" is determined in the measurement accuracy determination processing (NO at step S70), the processing unit 200 determines saving (unnecessary) (step S98), overwrites the previous location direction 516 with the current location direction 518 (step S100), and ends the saving necessity determination processing.

Returning to the flowchart in FIG. 14, if saving "necessary" is determined by the saving necessity determination processing (YES at step S120), the processing unit 200 additionally registers new data based on the latest location measurement information 512 in the memory point registration data 610 of the measurement data 602 and overwrites the latest location measurement information 512 on the latest memory point information 515 and registers the latest positioning point as a new memory point (step S122). If saving (unnecessary) is determined (NO at step S120), step S122 is skipped and the latest positioning point is not set as a memory point.

Then, the processing unit 200 executes distance computation processing (step S124).

Figure 17:
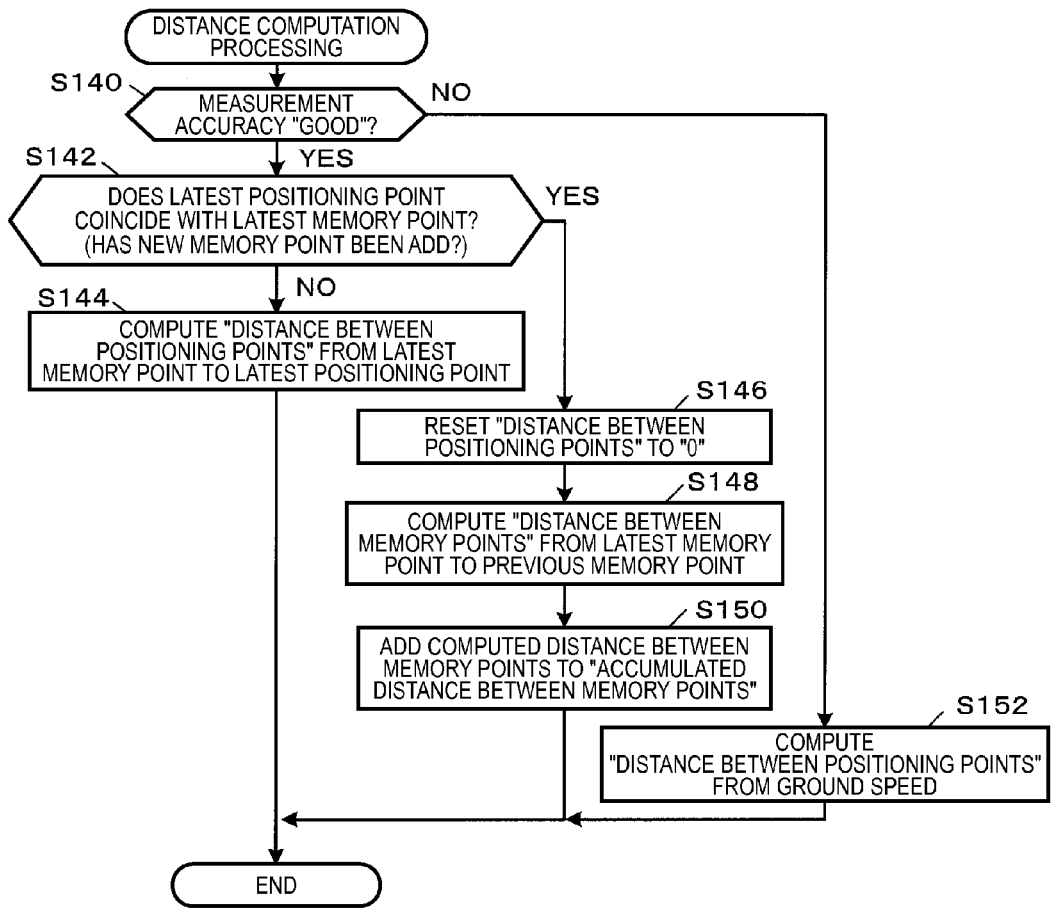
FIG. 17 is a flowchart for explanation of a flow of distance computation processing.

FIG. 17 is a flowchart for explanation of a flow of the distance computation processing in the embodiment. In the processing, the processing unit 200 first refers to the measurement accuracy flag 520.

If the measurement accuracy flag 520 is "1 (good)" (YES at step S140), the latest location measurement information 512 may be regarded as having sufficient measurement accuracy, and accordingly, the processing unit 200 subsequently determines whether or not the latest positioning point shown by the latest location measurement information 512 coincides with the latest memory point shown by the latest memory point information 515 (step S142).

If the latest positioning point does not coincide with the latest memory point (NO at step S142), the processing unit 200 computes the distance between positioning points 524 from the latest memory point (i.e., the most recent memory point) to the latest positioning point based on the location coordinates of the latest memory point information 515 and the location coordinates of the latest location measurement information 512 (step S144), and ends the distance computation processing.

If the latest positioning point coincides with the latest memory point (YES at step S142), the processing unit 200 resets the distance between positioning points 524 to "0" (step S146), then, computes the distance between memory points 528 from the latest memory point registered in the measurement data 602 to the previous memory point in the order of registration (step S148), adds the computed distance between memory points 528 to the accumulated distance between memory points 530 (step S150), and ends the distance computation processing.

On the other hand, at step S140, in the first place, if the latest location measurement information is judged with the measurement accuracy "no good" (NO at step S140), the unit computes a predicted location based on the ground speed V and the velocity direction Dv of the previous location measurement information 514, computes the distance from the previous positioning point shown by the previous location measurement information 514 to the predicted location, sets the distance to the distance between positioning points 524 (step S152), and ends the distance computation processing. Note that, in the embodiment, the measurement period is one second and the value of the ground speed V of the previous location measurement information 514 may be used as the distance between positioning points 524 without change.

Returning to the flowchart in FIG. 14, the processing unit 200 overwrites the value of the accumulated travel distance 532 on the previous accumulated travel distance 533, then, adds up the distance between positioning points 524 and the accumulated distance between memory points 530 updated by the distance computation processing and updates the accumulated travel distance 532 (step S170), and updates the display of the updated accumulated travel distance 532 (step S172: see the accumulated travel distance display 6 in FIG. 1).

Then, the processing unit 200 compares the start time and date of measurement 606 of the measurement data 602 with the positioning time and date of the latest location measurement information 512 and newly computes and updates the lapse time 534, and updates the display of the lapse time 534 in the image display unit 360 (step S174: see the lapse time display 8 in FIG. 1).

Then, the processing unit 200 refers to the distance memory period timer 538, if the distance memory period comes (YES at step S176), associates and adds the value of the current accumulated travel distance 532 and the ground speed V and the height H contained in the latest location measurement information 512 to the distance history data 620 of the measurement data 602 (step S178).

Then, the processing unit 200 executes section measurement processing (step S180).

Figure 18:
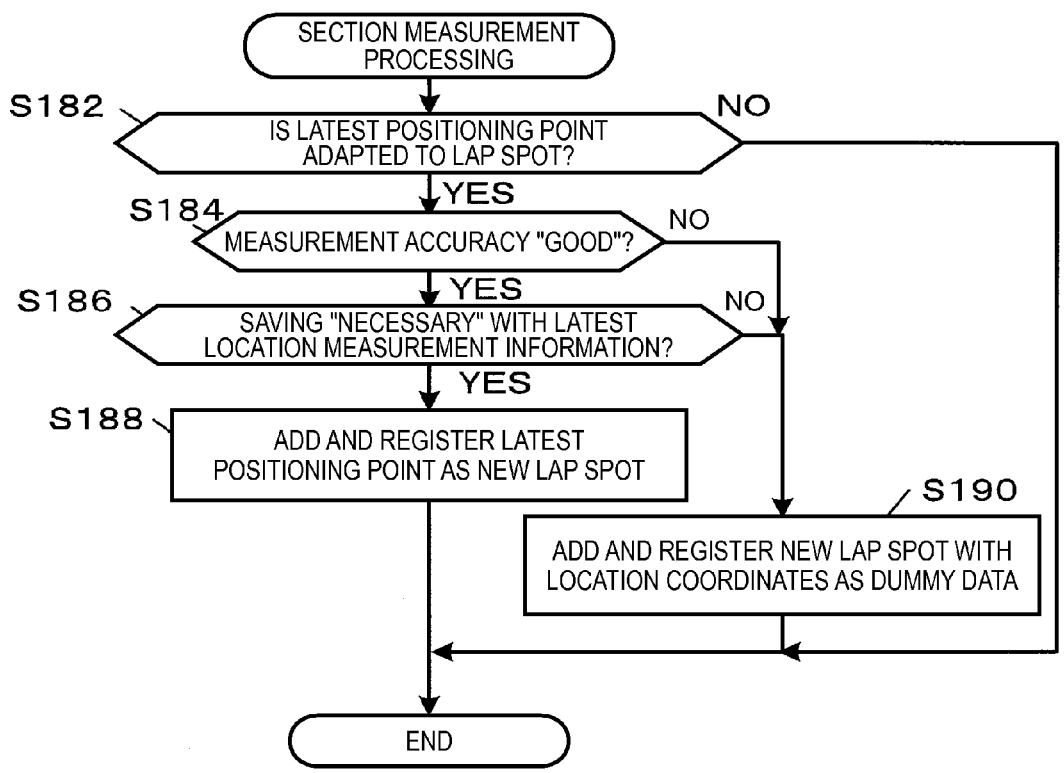
FIG. 18 is a flowchart for explanation of a flow of section measurement processing.

FIG. 18 is a flowchart for explanation of a flow of the section measurement processing in the embodiment. In the processing, the processing unit 200 of the electronic apparatus 2 first determines whether or not the latest positioning point shown by the latest location measurement information 512 satisfies an adaptation condition as the section end point of section measurement, i.e., the lap spot (step S182). The adaptation condition of the embodiment is "first positioning point at which difference between accumulated travel distance 532 and previous accumulated travel distance 533 increases by 1 km or more", however, another condition may be set.

Then, if the latest positioning point is determined to be adapted to the lap spot (YES at step S182) and the measurement accuracy is "good" (YES at step S184) and saving is "necessary" (YES at step S186), the processing unit 200 newly adds and registers data of the lap spot to the lap data 630 of the measurement data 602 (step S186). In this regard, the lapse time 534 is overwritten on the newly registered section time information 634, and the location information of the latest location measurement information 512 is overwritten on the newly registered location coordinates 636. Then, the processing unit 200 ends the lap registration processing.

Conversely, if the latest positioning point is adapted to the lap spot (YES at step S182), but the measurement accuracy "no good" (NO at step S184) or saving "unnecessary" (NO at step S186) is determined, the processing unit 200 newly adds the data of the lap spot to the lap data 630, stores predetermined dummy data that means "undetermined" ("NULL" in the example of FIG. 9) with respect to the location coordinates 636 (step S190), and ends the section measurement processing.

Returning to the flowchart in FIG. 14, the processing unit 200 repeats steps S28 to S180 until the unit detects the measurement end operation (NO at step S200). Then, if detecting the measurement end operation (YES at step S200), the unit acquires the location measurement information from the measurement unit 102, adds and registers the last memory point based on the acquired location measurement information to the memory point registration data 610 (step S202), and ends the measurement processing.

Returning to the flowchart in FIG. 13, if detecting communication connection with the data uploading device 50 (YES at step S250), the processing unit 200 of the electronic apparatus 2 transmits the measurement data 602 that has not been transmitted stored in the memory unit 500 (step S252). Note that the communication connection between the electronic apparatus 2 and the data uploading device 50 is realized by establishment of an ad hoc network by near field communication or connection detection of the USB cable 42.

Next, the operations of the data uploading device 50 and the data analyzer 70 will be explained.

Figure 19:
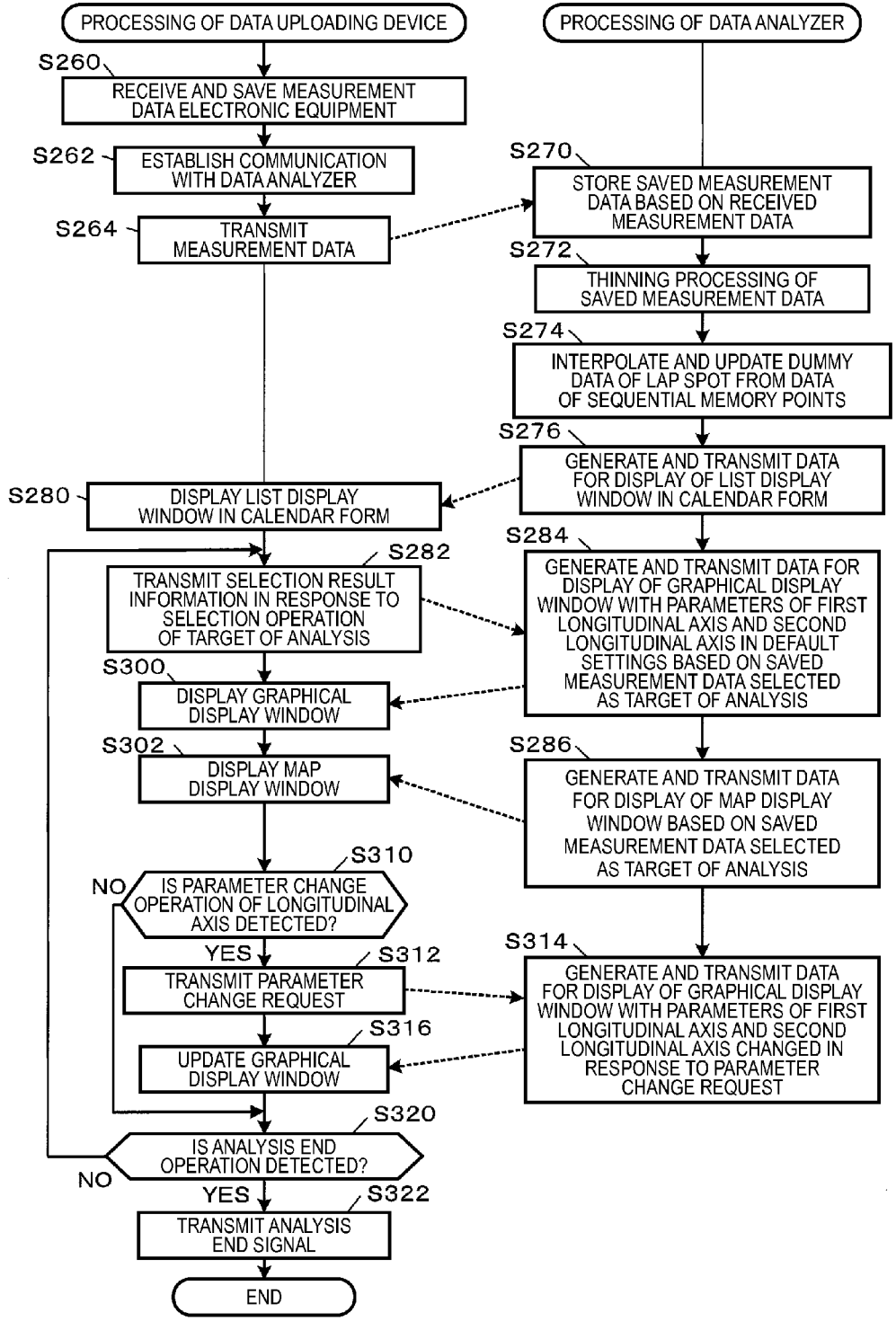
FIG. 19 is a flowchart for explanation of a flow of processing relating to uploading of data to display of data analysis.

FIG. 19 is a flowchart for explanation of a flow of processing relating to uploading of data to display of data analysis of the embodiment.

When receiving the measurement data 602 from the electronic apparatus 2, the data uploading device 50 once saves the data in the IC memory 60 or the like of itself (step S260). Then, the device connects to the Internet 9 for establishment of data communication with the data analyzer 70 (step S262), and transmits the measurement data 602 received from the electronic apparatus 2 with user registration information prepared in advance to the data analyzer 70 (step S264).

The data analyzer 70 may also serve as a server of a website requiring user registration, for example. In this case, suppose that information for user identification of the website is registered in advance in the electronic apparatus 2 and the data uploading device 50, and data transmission to the data analyzer 70 requires user authentication.

The data analyzer 70 associates the measurement data 603 received from the data uploading device 50 with the user ID 609 and stores and saves the data as the saved measurement data 603 (step S270: see FIG. 12).

Then, the processing unit 200v of the data analyzer 70 performs thinning processing of the saved measurement data 603 to the suitable number for graphical display (step S272). Specifically, the unit thins the number of history records of the distance history data 620 to be equal to the number of scale marks of the lateral axis (time axis) of the graphical display by computing an average value from the respective parameter values (e.g., the accumulated travel distance 624, the ground speed 626, etc.) of a plurality of sequential history records and replacing the plurality of sequential history records by one history record, for example. Concurrently, the unit generates and adds the thinning information 608 to the saved measurement data 603.

Then, the data analyzer 70 extracts the lap spots at which the dummy data is set to the location coordinates 636 in the lap data 630 from the saved measurement data 603, obtains the location coordinates 636 of the extracted lap spots by interpolation computation based on the location coordinates 616 of the section time information 634 of the extracted lap spots and the memory points with the sequential lapse times 614 or the like, and overwrites and updates the dummy data by interpolation values (step S274: see FIG. 5).

Then, the data analyzer 70 generates a list display window data (e.g., image data, script data, etc.) for display of a selection window (list display window in calendar form W2 in FIG. 6) for the user to select one of the saved measurement data 603 that have been received and saved from the data uploading device 50 as a target of analysis on the data uploading device 50, and transmits the data to the data uploading device 50 (step S276).

The data uploading device 50 receives the data and displays the list display window in calendar form W2 (step S280). Then, if detecting the selection operation of the measurement data as the target of analysis with the list display window in calendar form W2 being displayed, the data uploading device 50 transmits selection result information to the data analyzer 70 (step S282).

When receiving the selection result information, the data analyzer 70 generates the graphical display window data for display of the graphical display window W4 on the touch panel 52 using the parameters of the first longitudinal axis and the second longitudinal axis of the graph as initial settings based on the saved measurement data 603 selected as the target of analysis, and transmits the data to the data uploading device 50 (step S284). Further, the analyzer generates the map display window data for display of the map display window on the touch panel 52, and transmits the data to the data uploading device 50 (step S286).

The data uploading device 50 receives the graphical display window data and allows the touch panel 52 to display the graphical display window W4 (step S300: see FIG. 7), and receives the map display window data and allows the touch panel 52 to display the map display window W6 (step S302: see FIG. 8).

Then, if detecting a change operation of the parameter as the longitudinal axis of the graph with the graphical display window W4 being displayed (YES at step S310), the data uploading device 50 transmits a change request of the parameter to the data analyzer (step S312). If receiving the request, the data analyzer 70 changes the parameter setting of the longitudinal axis of the graph in response to the received change request, regenerates the graphical display window data, and transmits the data to the data uploading device 50 (step S314). The data uploading device 50 receives the regenerated graphical display window data and updates the graphical display window W4 (step S316).

If detecting the predetermined analysis end operation (YES at step S320), the data uploading device 50 transmits an analysis end signal to the data analyzer 70 (step S322), and ends processing relating to uploading of data and display of the data analysis result.

As described above, according to the embodiment, the data volume of the measurement data 602 may be reduced by thinning of the location measurement information. Therefore, even when the memory capacity and the battery capacity are substantially equal to those mounted on products in related art that has realized reduction in size and weight, by application of the invention, storage of the measurement data over the longer distance and longer period may be realized.

Modified Examples

The embodiment to which the invention is applied has been explained, however, the application embodiment of the invention is not limited to that, but various additions, omissions, changes of component elements may be appropriately made.

Figure 20:
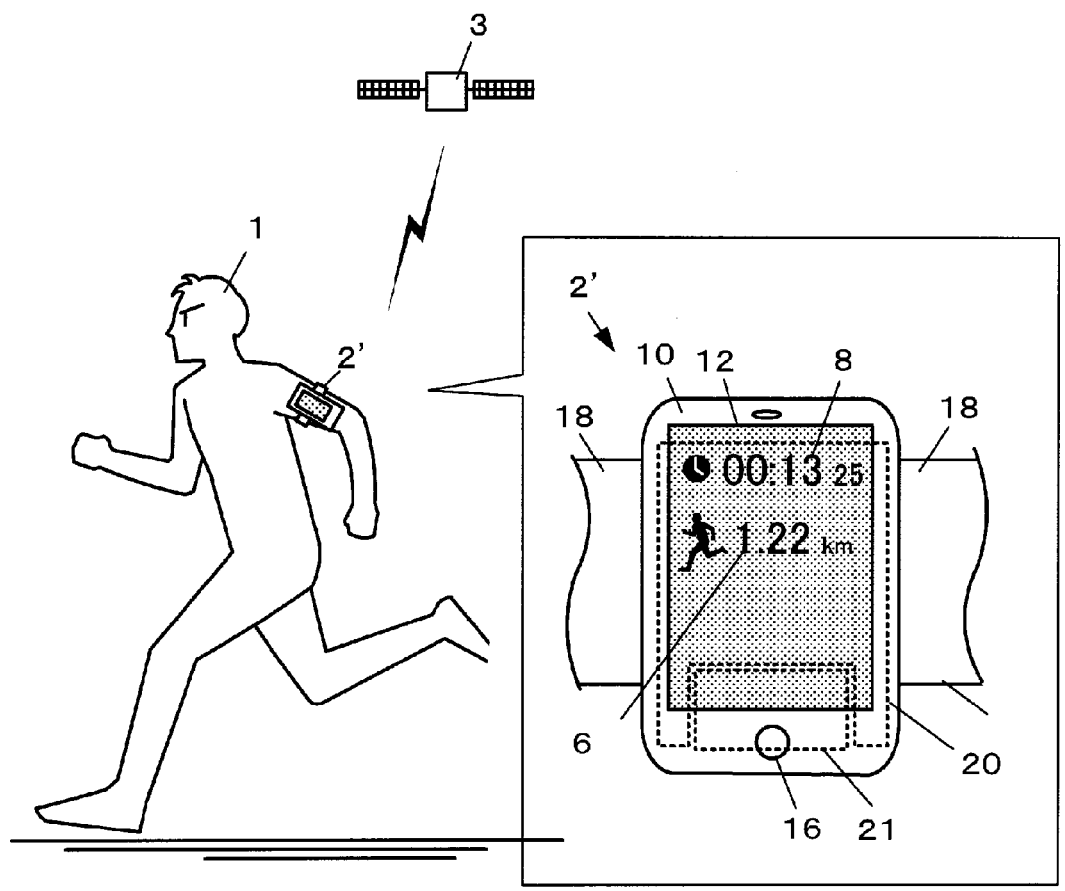
FIG. 20 shows a modified example of the wearable electronic apparatus.

For example, in the embodiment, the electronic apparatus 2 has been an apparatus suitable for wearing on the wrist of the user as an example, however, where on the body the apparatus is worn may be appropriately changed. For example, as shown by an electronic apparatus 2' in FIG. 20, an apparatus assumed to be worn mainly on the upper arm with the band 18 may be designed. In this case, the design of the apparatus may be appropriately set, not limited to the wristwatch type, but may be a tablet type.

Further, in the embodiment, the data uploading device 50 and the data analyzer 70 have been explained as separate devices, however, they may be integrated. For example, the data uploading device 50 may be formed to execute the processing in the data analyzer 70.

Furthermore, the explanation that the GPS is used for the location measurement system has been made, however, other satellite positioning system including WAAS (Wide Area Augmentation System), QZSS (Quasi Zenith Satellite System), GLONASS (GLObal Navigation Satellite System), and GALILEO may be employed.

The entire disclosure of Japanese Patent Application No. 2012-175311, filed Aug. 7, 2012 is expressly incorporated by reference herein.

What is claimed is:

1. A wearable electronic apparatus comprising:
a memory;
  a location measurement module for receiving one or more signals from a location measurement system; and
  a processor coupled to the memory and the location measurement module, wherein the processor is adapted to:
  measure a location with a predetermined period based on the one or more received signals;
  compute an accumulated travel distance based on the measured location;
  determine whether the measured location is accurate or not;
  determine whether the measured location is necessary or not with reference to a previous measured location,
  when the measured location is accurate and necessary, determine that the measured location is to be saved in the memory;
  when the measured location is not accurate or not necessary, determine the measured location is not to be saved in the memory;
  determine whether the measured location corresponds to a section measurement point or not,
  control the memory to store the measured location when the measured location is determined to be saved;
  control the memory to store a dummy data instead of the measured location when the measured location corresponds to the section measurement point and determined not to be saved, and
  control the memory to output data stored in the memory corresponding to the measured location to an external device.

2. The apparatus according to claim 1, wherein the processor is further adapted to determine that the measured location is to be saved when a direction change condition showing that a movement direction has changed based on the measured location is satisfied.

3. The apparatus according to claim 2, wherein the processor is further adapted to measure the location based on satellite signals and to measure at least the movement direction based on Doppler of the satellite signals, and to determine whether or not the direction change condition is satisfied based on the movement direction.

4. The apparatus according to claim 3, wherein the processor is further adapted to determine that the measured location is not to be saved when the movement direction and a travel direction based on the measured location and the previous measured location do not satisfy a predetermined approximate condition.

5. The apparatus according to claim 1, wherein the processor is further adapted to control the memory to store the accumulated travel distance after a longer time interval than the predetermined period in a temporal sequence, and
control the memory to output data of one or more accumulated travel distances stored in the memory to the external device.

6. The apparatus according to claim 1, wherein the processor is further adapted to,
when the measured location corresponds to the section measurement point, control the memory to store a lapse time from a start of computation of the accumulated travel distance, or a time taken for traveling from a previous section measurement point to the section measurement point, in correspondence with the measured location or the dummy data; and
control the memory to output data of the lapse time or the time taken for traveling stored in the memory to the external device.

7. The apparatus according to claim 1, wherein the section measurement point comprises a lap point.

8. A travel record control method executed by an electronic apparatus worn on a body, comprising:
receiving one or more signals from a location measurement system;
measuring a location with a predetermined period based on the one or more received signals;
computing an accumulated travel distance based on the measured location;
determining whether the measured location is accurate or not;
determining whether the measured location is necessary or not with reference to a previous measured location;
when the measured location is accurate and necessary, determine Caving the measured location is to be saved in a memory;
when the measured location is not accurate or not necessary, determining the measured location is not to be saved in the memory;
determining whether the measured location corresponds to a section measurement point or not;
controlling the memory to store the measured location when the measured location is determined to be saved in the memory;
control the memory unit to store a dummy data instead of the measured location data when the measured location corresponds to the section measurement point and determined not to be saved; and
controlling the memory to output data corresponding to the measured location to an external device.

* * * * *